United States Patent
Shih et al.

(10) Patent No.: US 8,715,575 B2
(45) Date of Patent: May 6, 2014

(54) LEAD-FREE PIEZOELECTRIC CERAMIC FILMS AND A METHOD FOR MAKING THEREOF

(71) Applicants: Wei-Heng Shih, Bryn Mawr, PA (US); Wan Y. Shih, Bryn Mawr, PA (US); Huidong Li, Richland, WA (US)

(72) Inventors: Wei-Heng Shih, Bryn Mawr, PA (US); Wan Y. Shih, Bryn Mawr, PA (US); Huidong Li, Richland, WA (US)

(73) Assignee: Drexel University, Philadelphia, PA (US)

( * ) Notice: Subject to any disclaimer, the term of this patent is extended or adjusted under 35 U.S.C. 154(b) by 0 days.

(21) Appl. No.: 13/927,962

(22) Filed: Jun. 26, 2013

(65) Prior Publication Data

US 2014/0004000 A1 Jan. 2, 2014

Related U.S. Application Data

(62) Division of application No. 13/494,772, filed on Jun. 12, 2012, now Pat. No. 8,496,870, which is a division of application No. 12/741,790, filed as application No. PCT/US2008/084190 on Nov. 20, 2008, now Pat. No. 8,241,569.

(60) Provisional application No. 60/989,902, filed on Nov. 23, 2007.

(51) Int. Cl.
 *G01N 15/00* (2006.01)

(52) U.S. Cl.
 USPC ....... 422/82.01; 422/50; 422/82.02; 501/134; 501/136; 501/137; 501/138; 264/614

(58) Field of Classification Search
 USPC ............ 422/68.1, 50, 82.01, 82.02; 501/134, 501/136, 137, 138; 252/62.9; 264/614, 650
 See application file for complete search history.

(56) References Cited

U.S. PATENT DOCUMENTS

| | | |
|---|---|---|
| 3,205,464 A | 9/1965 | Schwartz |
| 4,302,694 A | 11/1981 | Fujishima et al. |
| 4,349,762 A | 9/1982 | Kitamura et al. |
| 4,363,993 A | 12/1982 | Nishigaki et al. |
| 4,528,502 A | 7/1985 | Rocha |
| 4,649,312 A | 3/1987 | Robin et al. |
| 4,802,371 A | 2/1989 | Calderara et al. |
| 5,054,323 A | 10/1991 | Hubbard et al. |

(Continued)

FOREIGN PATENT DOCUMENTS

| | | |
|---|---|---|
| EP | 0631319 A1 | 12/1994 |
| EP | 1536227 A2 | 6/2005 |

(Continued)

OTHER PUBLICATIONS

Amanuma, K. et al., "Crystallization behavior of sol-gel derived Pb(Zr,Ti)O3 thin films and the polarization switching effect on film microstructure", Appl. Phys. Lett., 65(24): 3140-3142 (1994).

(Continued)

*Primary Examiner* — Brian J Sines
(74) *Attorney, Agent, or Firm* — Mendelsohn, Drucker & Dunleavy, P.C.

(57) ABSTRACT

This invention relates to a method of making lead-free piezoelectric ceramic films. Specifically, the invention is directed to a method for fabricating lead-free piezoelectric free standing films having enhanced piezoelectric properties. The films may be used for a number of applications including incorporation in microelectronic devices such as energy harvesting devices and sensor technologies.

20 Claims, 11 Drawing Sheets

(56) References Cited

U.S. PATENT DOCUMENTS

| | | | |
|---|---|---|---|
| 5,313,535 | A | 5/1994 | Williams |
| 5,334,835 | A | 8/1994 | Nakayama et al. |
| 5,338,999 | A | 8/1994 | Ramakrishnan et al. |
| 5,445,008 | A | 8/1995 | Wachter et al. |
| 5,475,318 | A | 12/1995 | Marcus et al. |
| 5,503,010 | A | 4/1996 | Yamanaka |
| 5,553,486 | A | 9/1996 | Bonin |
| 5,626,728 | A | 5/1997 | Ramakrishnan et al. |
| 5,689,063 | A | 11/1997 | Fujiu et al. |
| 5,719,324 | A | 2/1998 | Thundat et al. |
| 5,780,727 | A | 7/1998 | Gimzewski et al. |
| 5,807,758 | A | 9/1998 | Lee et al. |
| 5,866,807 | A | 2/1999 | Elings et al. |
| 5,874,126 | A | 2/1999 | Kahn et al. |
| 5,948,993 | A | 9/1999 | Ting et al. |
| 5,966,787 | A | 10/1999 | Nakayama et al. |
| 5,996,412 | A | 12/1999 | Hansen |
| 6,075,585 | A | 6/2000 | Minne et al. |
| 6,278,379 | B1 | 8/2001 | Allen et al. |
| 6,280,396 | B1 | 8/2001 | Clark |
| 6,289,717 | B1 | 9/2001 | Thundat et al. |
| 6,336,366 | B1 | 1/2002 | Thundat et al. |
| 6,422,069 | B1 | 7/2002 | Shimizu et al. |
| 6,458,327 | B1 | 10/2002 | Vossmeyer et al. |
| 6,465,368 | B2 | 10/2002 | Inoue et al. |
| 6,589,727 | B1 | 7/2003 | Klenerman et al. |
| 6,621,080 | B2 | 9/2003 | Yamamoto |
| 6,734,425 | B2 | 5/2004 | Hantschel et al. |
| 6,781,285 | B1 | 8/2004 | Lazarus et al. |
| 6,903,491 | B2 | 6/2005 | Irie et al. |
| 6,992,421 | B2 | 1/2006 | Ikeda et al. |
| 7,055,378 | B2 | 6/2006 | Su et al. |
| 7,083,270 | B2 | 8/2006 | Torii et al. |
| 7,084,554 | B2 | 8/2006 | Xu et al. |
| 7,104,134 | B2 | 9/2006 | Amano et al. |
| 7,195,909 | B2 | 3/2007 | Klenerman et al. |
| 7,263,874 | B2 | 9/2007 | Fitch et al. |
| 7,744,773 | B2 | 6/2010 | Shih et al. |
| 2002/0094528 | A1 | 7/2002 | Salafsky |
| 2002/0117659 | A1 | 8/2002 | Lieber et al. |
| 2002/0155303 | A1 | 10/2002 | Wielstra et al. |
| 2003/0032293 | A1 | 2/2003 | Kim et al. |
| 2003/0068655 | A1 | 4/2003 | Bottomley et al. |
| 2003/0194697 | A1 | 10/2003 | Klenerman et al. |
| 2003/0224551 | A1 | 12/2003 | Kim et al. |
| 2003/0235681 | A1 | 12/2003 | Sebastian et al. |
| 2004/0022677 | A1 | 2/2004 | Wohlstadter et al. |
| 2004/0265664 | A1 | 12/2004 | Badding et al. |
| 2005/0112621 | A1 | 5/2005 | Kim et al. |
| 2005/0114045 | A1 | 5/2005 | Giurgiutiu et al. |
| 2005/0199047 | A1 | 9/2005 | Adams et al. |
| 2005/0277852 | A1 | 12/2005 | Shih et al. |
| 2005/0287680 | A1 | 12/2005 | Venkatasubbarao et al. |
| 2006/0053870 | A1 | 3/2006 | Berndt |
| 2006/0217893 | A1 | 9/2006 | Li et al. |
| 2006/0223691 | A1 | 10/2006 | Shih et al. |
| 2006/0228657 | A1 | 10/2006 | Masters et al. |
| 2006/0257286 | A1 | 11/2006 | Adams |
| 2007/0089515 | A1 | 4/2007 | Shih et al. |
| 2007/0141721 | A1 | 6/2007 | Vafai et al. |
| 2007/0169553 | A1 | 7/2007 | Mutharasan |
| 2007/0218534 | A1 | 9/2007 | Klenerman et al. |
| 2008/0034840 | A1 | 2/2008 | Mutharasan |
| 2008/0035180 | A1 | 2/2008 | Mutharasan |
| 2009/0007645 | A1 | 1/2009 | Shih et al. |
| 2009/0053709 | A1 | 2/2009 | Mutharasan |
| 2009/0078023 | A1 | 3/2009 | Mutharasan |
| 2009/0203000 | A1 | 8/2009 | Mutharasan |
| 2010/0239463 | A1 | 9/2010 | Shih et al. |

FOREIGN PATENT DOCUMENTS

| | | |
|---|---|---|
| JP | 3093849 B2 | 4/2000 |
| JP | 2003-298131 A | 10/2003 |
| JP | 2004-265899 A | 9/2004 |
| JP | 2007-67125 A | 3/2007 |
| WO | 98/50773 A2 | 11/1998 |
| WO | 2004/061991 A1 | 7/2004 |
| WO | 2005/043126 A2 | 5/2005 |
| WO | 2006/031072 A1 | 3/2006 |
| WO | 2007/087328 A2 | 8/2007 |
| WO | 2007/133619 A1 | 11/2007 |
| WO | 2008/020903 A2 | 2/2008 |
| WO | 2008/021187 A2 | 2/2008 |
| WO | 2008/021189 A2 | 2/2008 |
| WO | 2008/101199 A1 | 8/2008 |
| WO | 2009/014830 A1 | 1/2009 |
| WO | 2009/035732 A2 | 3/2009 |
| WO | 2009/046251 A2 | 4/2009 |
| WO | 2009/035732 A3 | 7/2009 |

OTHER PUBLICATIONS

Ammari, H. et al., "T-Scan Electrical Impedance Imaging System for Anomaly Detection", Siam J. Appl. Math., 65(1): 252-266 (2004).

Baselt, D. R. et al., "Biosensor based on force microscope technology", J. Vac. Sci. Technol. B, 14(2): 789-793 (1996).

Birnie, III, D. P. et al., "Coating uniformity and device applicability of spin coated sol-gel PXT films", Microelectronic Engineering, 29: 189-192 (1995).

Bondoux, C. et al., "MgO insulating films prepared by sol-gel route for SiC substrate", J. Europe. Ceramic Soc., 25: 2795-2798 (2005).

Brito, R. et al., "Adsorption of 3-mercaptopropyltrimethoxysilane and 3-aminopropyltrimethoxysilane at platinum electrodes", J. Electroanalytical Chem., 520: 47-52 (2002).

Campbell, G.A., et al., "Piezoelectric excited millimeter-sized cantilever (PEMC) sensor detects *Escherichia coli* O157:H7 in two-hour incubated samples at 4 CFU per gram of beef," J. of Rapid Methods and Automation in Mirobiology, 1-39.

Campbell, G.A., et al., "Detection and quantification of proteins using self-excited PZT-glass millimeter-sized cantilever," Biosensors and Bioelectronics, 26-36.

Campbell, G.A., "Piezoelectric-excited millimeter-sized cantilever (PEMC) sensors detect *Bacillus anthracis* at 300 spores/mL," Biosensors and Bioelectronics, 37-45.

Campbell, G.A., et al., "kinetics of *Bacillus anthracis* spore binding to antibody functionalized PEMC sensors in presence of *Bacillus thuringiensis* and *Bacillus cereus*," J. Publications, Am. Chem. Soc. 25 pages.

Campbell, G.A., et al., "*Escherichia coli* O157:H7 detection limit of millimeter-sized PZT cantilever sensors in 700 cells/mL," Analytical Sci., 11-13.

Campbell, G.A., et al., "Detection of pathogen *Escherichia coli* O157:H7 using self-excited PZT-glass microcantilevers," Biosensors and Boelectronics, 14-25.

Campbell, G.A., "Detection of staphylococcus enterotoxin B at pictogram levels using piezoelectric-excited millimeter-sized cantilever sensors," Submitted on line to J. of Analytical Chem., 1-24.

Campbell, G.A., et al., "Detect *Escherichia coli* O157:H7 in ground beef samples using piezoelectric excited millimeter-sized cantilever (PEMC) sensors," Submitted on-line to Biosensors and Bioelectronics, 2-34.

Campbell, G.A., et al., "A method for measuring *Escherichia coli* O157:H7 at 1 cell/mL in 1 liter sample using antibody functional piezoelectric-excited millimeter sized cantilever sensor," Paper submitted on-line to J. of Analytical Chemistry. 1-23.

Capobianco, J. A., et al., "Methyltrimethoxysilane- insulated piezoelectric microcantilevers for direct, all-electrical biodetection in buffered aqueous solutions", Rev. Sci. Instrum., 77: 125105-1-125105-6 (2006).

Capobianco, J. A., et al., "3-mercaptopropyltrimethoxysilane as insulating coating and surface for protein immobilization for piezoelectric microcantilever sensors", Rev. Sci. Instrum., 78: 046106-1-046106-3 (2007).

Carlier, S. G., et al., "Elastography", J. Cardiovasc Risk, 9(5): 237-245 (2002).

(56) References Cited

OTHER PUBLICATIONS

Carr, D.W., et al., "Fabrication of nanoelectromechanical systems in single crystal silicon using silicon on insulator substrates and electron beam lithography," J. Vac. Sci. Technology, B, 5(6), 2760-2763.
Che, G. et al., "Molecular recognition based on (3-mercaptopropyl) trimethoxysilane modified gold electrodes", J. Electroanalytical Chem., 417: 155-161 (1996).
Chen, G. Y. et al., "Adsorption-induced surface stress and its effects on resonance frequency of microcantilevers", J. Appl. Phys., 77(8): 3618-3622 (1995).
Chen, X. et al., "Electrochemical and Spectroscopic Characterization of Surface Sol-Gel Processes", Langmuir, 20 (20): 8762-8767 (2004).
Cho, S. H. et al., "Micro-scale metallization on flexible polyimide substrate by Cu electroplating using SU-8 photoresist mask", Thin Solid Films, 475: 68-71 (2005).
Duval, F.F.C. et al., "Stable TiO2/Pt electrode structure for lead containing ferroelectric thick films on silicon MEMS structures", Thin Solid Films, 444: 235-240 (2003).
Feili, D. et al., "Encapsulation of organic field effect transistors for flexible biomedical microimplants", Sensors and Actuators, A120: 101-109 (2005).
Ferrini, R. et al., "Screening Mammography for Breast Cancer: American College of Preventive Medicine Practice Policy Statement", www.acpm.org/breast, pp. 1-4 (2005).
Fritz, J. et al., "Translating Biomolecular Recognition into Nanomechanics", Science, 288: 316-318 (2000).
Fung, Y. S. et al., "Self-Assembled Monolayers as the Coating in a Quartz Piezoelectric Crystal Immunosensor to Detect *Salmonella* in Aqueous Solution", Anal. Chem., 73: 5302-5309 (2001).
Gao, L. et al., "Imaging of the elastic properties of tissue: A review", Ultrasound in Med. & Biol., 22(8): 959-977 (1996). Abstract Only.
Greenleaf, J. F. et al., "Selected Methods for Imaging Elastic Properties of Biological Tissues", Annu. Rev. Biomed. Eng., 5: 57-78 (2003).
Gu, H. et al., "Single-Calcination Synthesis of Pyrochlore-Free 0.9Pb(Mg1/3Nb2/3)O3-0.1PbTiO3 and Pb (Mg1/3Nb2/3)O3 Ceramics Using a Coating Method", J. Am. Ceram. Soc., 86(2): 217-221 (2003).
Haccart, T. et al., "Evaluation of niobium effects on the longitudinal piezoelectric coeffecients of Pb(Zr,Ti)O3 thin films", Appl. Phys. Lett., 76(22): 3292-3294 (2000).
Han, W. et al., "A magnetically driven oscillating probe microscope for operations in liquids", Appl. Phys. Lett., 69(26): 4111-4113 (1996).
Hiboux, S. et al., "Mixed titania-lead oxide seed layers for PZT growth on Pt(111): a study on nucleation, texture and properties", J. Europe. Ceram. Soc., 24: 1593-1596 (2004).
Hwang, I.H. et al., "Self-actuating biosensor using a piezoelectric cantilever and its optimization", Journal of Physics: Conference Series 34, pp. 362-367, 2006.
Hwang, K.S. et al., "In-situ quantitative analysis of a prostate-specific antigen (PSA) using a nanomechanical PZT cantilever", Lab Chip, 4: 547-552 (2004).
Ilic, B. et al., "Mechanical resonant immunospecific biological detector", Appl. Phys. Lett., 77(3): 450-452 (2000).
Itoh, T. et al., "Self-excited force-sensing microcantilevers with piezoelectric thin films for dynamic scanning force microscopy", Sensor and Actuators, A54:477-481 (1996).
Jung, S.K. et al., "Polymeric Mercaptosilane-Modified Platinum Electrodes for Elimination of Interferants in Glucose Biosensors", Anal. Chem., 68: 591-596 (1996).
Kanda, T. et al., "A flat type touch probe sensor using PZT thin film vibrator", Sensors and Actuators, 83: 67-75 (2000).
Katiyar, P. et al. "Electrical properties of amorphous aluminum oxide thin films", Acta Materialia, 53: 2617-2622 (2005).
Keller, A. et al., "Reliability of Computed Tomography Measurements of Paraspinal Muscle Cross-Sectional Area and Density in Patients With Chronic Low Back Pain", Spine, 28(13): 1455-1460 (2003).

Kelly, J. et al., "Effect of Composition on the Electromechanical Properties of (1-x)Pb(Mg1/3Nb2/3)O3-xPbTiO3 Ceramics" J. Am. Ceram. Soc., 80(4): 957-964 (1997).
Khabari, A. et al., "Partially ionized beam deposition of parylene" J. Non-Crystalline Solids, 351: 3536-3541 (2005).
Kim, S.H. et al., "Influence of Al2O3 diffusion barrier and PbTiO3 seed layer on microstructurel and ferroelectric charachteristics of PZT thin films by sol-gel spin coating method," Thin Solid Films, 305: 321-326 (1997).
Kim, S.J. et al., "Fabrication and Characterization of Pb(Zr,Ti)O3 Microcantilever for Resonance Sensors," Jpn. J. Appl. Phys., 42(3): 1475-1478 (2003).
Klissurska, R.D. et al. "Microstructure of PZT sol-gel films on Pt substrates with different adhesion layers," Microelectronic Engineering, 29: 297-300 (1995).
Kruse, S.A. et al., "Tissue characterization using magnetic resonance elastography: preliminary results," Phys. Med. Biol., 45: 1579-1590 (2000).
Kumar, V. et al., "A Simple System for the Preparation of Submicrometer Lead Titanate Powders by the Sol-Gel Method," J. Am. Ceram. Soc., 79(10): 2775-2778 (1996).
Kwok, CLK. et al., "Low temperature perovskite formation of lead zirconate titanate thin films by a seeding process," J. Mater. Res., 8(2): 339-344 (1993).
Lee, C. et al., "Sol-gel derived PZT force sensor for scanning force microscopy", Mater. Chem. Phys., 44: 25-29 (1996).
Lee, C. et al., "Self-excited piezoelectric PZT microcantilevers for dynamic SFM—with inherent sensing and actuating capabilities", Sensors and Actuators, A72: 179-188 (1999).
Lee, J. H. et al., "Label free novel electrical detection using micromachined PZT monolithic thin film cantilever for the detection of C-reactive protein", Biosensors and Bioelectronics, 20: 269-275 (2004).
Lee, J. H. et al., "Effect of mass and stress on resonant frequency shift of functionalized Pb(Zr0.52Ti0.48)O3 thin film microcantilever for the detection of C-reactive protein", Appl. Phys. Lett., 84(16): 3187-3189 (2004).
Lee, J. H. et al., "Immunnoassay of prostate-specific antigen (PSA) using resonant frequency shift of piezoelectric nanomechanical microcantilever", Biosensors and Bioelectronics, 20: 2157-2162 (2005).
Lee, S. S. et al., "Self-Excited Piezoelectric Cantilever Oscillators", The 8th International Conference on Solid-State Sensors and Actuators, and Eurosensors IX, Stockholm, Sweden: 417-420 (1995).
Lee, Y. et al., "A Piezoelectric Micro-Cantilever Bio-Sensor Using the Mass-Microbalancing Technique With Self-Excitation", The 13th International Conference on Solid-State Sensors, Actuators, and Microsystems, Seoul, Korea: 644-647 (2005).
Li, S. et al., "The intrinsic nature of nonlinear behavior observed in lead zirconate titanate ferroelectric ceramic", J. Appl. Phys., 69(10): 7219-7224 (1991).
Li, X. et al., "Detection of water-ice transition using a lead zirconate titanate/brass transducer", J. Appl. Phys., 92(1): 106-111 (2002).
Lin, Z. et al., "Operation of an Ultrasensitive 30-MHz Quartz Crystal Microbalance in Liquids", Anal. Chem., 65(11): 1546-1551 (1993).
Liu, W. et al., "Preparation and orientation control of Pb1.1(Zr0.3Ti0.7)O3 thin films by a modified sol-gel process", Mat. Lett., 46: 239-243 (2000).
Luo, H. et al., "Synthesis of PMN and 65PMN-35PT Ceramics and Films by a New Suspension Method", Ceramic Transactions, 136, (2003), 251-260.
Luo, H. et al., "Comparison in the Coating of Mg(OH)2 on Micron-Sized and Nanometer-Sized Nb2O5 Particles", Int. J. Appl. Ceram. Technol., 1(2): 146-154 (2004).
Luo, H., "Colloidal Processing of PMN-PT Thick Films for Piezoelectric Sensor Applications", A Thesis Submitted to the Faculty of Drexel University in Jun. 2005.
Maki, K. et al., "Evaluation of Pb(Kr,Ti)O3 Films Derived from Propylene-Glycol-Based Sol-Gel Solutions", Jpn. J. Appl. Phys., 39(9B): 5421-5425 (2000).
Maraldo, D. et al., "Resonant-mode millimeter sized cantilever biosensor for continuous detection of proteins and pathogens in flowing liquids," Dept. of Chem. and Biological Eng., 1-21 (2006).

(56) References Cited

OTHER PUBLICATIONS

Matsui, Y. et al., "Highly Oxidation-Resistant TiN Barrier Layers for Ferroelectric Capacitors", Jpn. J. Appl. Phys., 36 (3B): 1586-1588 (1997).
Mazza, E. et al., Biomechanics, http://www.zfm.ethz.ch/e/res/bio/, 1-10 (Feb. 24, 2009).
McGovern, J.P. et al., "Real-Time *Salmonella* Detection Using Lead Zirconate Titanate-Titanium Microcantilevers", Mater. Res. Soc. Symp. Proc., 845: AA3.8.1-AA3.8.6 (2005).
Mueller, V. et al., "Nonlinearity and scaling behavior in donor-doped lead zirconate titanate piezoceramic", Appl. Phys. Lett., 72(21): 2692-2694 (1998).
Mulvihill, M. L. et al., "The Role of Processing Variables in the Flux Growth of Lead Zinc Niobate-Lead Titanate Relaxor Ferroelectric Single Crystals", Jpn. J. Appl. Phys., 35(7): 3984-3990 (1996).
Niedziolka, J. et al., "Charaterisation of gold electrodes modified with methyltrimethoxysilane and (3-mercaptopropyl)trimethoxysilane sol-gel processed films", J. Electroanalytical Chem., 578: 239-245 (2005).
Nguyen, L. T. T. et al., "Synthesis and characterization of a photosensitive polyimide precursor and its photocuring behavior for lithography applications", Optical Materials, 29: 610-618 (2007).
Oden, P. I. et al., "Viscous drag measurements utilizing microfabricated cantilevers", Appl. Phys. Lett., 68(26): 3814-3816 (1996).
Ohnmacht, M. et al., "Microcoils and microrelays—an optimized multilayer fabrication process", Sensors and Actuators, 83: 124-129 (2000).
Park, G.T. et al., "Measurement of piezoelectric coefficients of lead zirconate titanate thin films by strain-monitoring pneumatic loading method", Appl. Phys. Lett., 80(24): 4606-4608 (2002).
Park, S.E. et al., "Ultrahigh strain and piezoelectric behavior in relaxor based ferroelectric single crystals", J. Appl. Phys., 82(4): 1804-1811 (1997).
Piezo Systems, Inc., "Piezoceramine Sheets and Their Properties", Piezo Systems, Inc. Catalog: 1-3 (2007).
Pons, T. et al., "Solution-phase single quantum dot fluorescence resonance energy transfer", J. Amer. Chem. Soc., 128(47): 15324-15331 (2006). Abstract Only.
Ren, W. et al., "Non linear strain and DC bias induced piezoelectric behaviour of electrostrictive lead magnesium niobate-lead titanate ceramics under high electric fields", J. Phys. D: Appl. Phys., 35: 1550-1554 (2002).
Ren, W. et al., "Nonlinear behavior of piezoelectric lead zinc niobate-lead titanate single crystals under ac electric fields and dc bias", Appl. Phys. Lett., 83(25): 5268-5270 (2003).
Rosenberg, RD et al., "Effects of age, breast density, ethnicity and estrogen replacement therapy on screening mammographic sensitivity and cancer stage at diagnosis: review of 183,134 screening mammograms in Albuquerque, New Mexico", Radiology, 209(2): 511-5118 (1998). Abstract Only.
Saito, Y. et al., "Lead-free piezoceramics", Nature, 432: 84-87 (2004).
Schemmel, A. et al., "Single molecule force spectrometer with magnetic force control and inductive detection", Rev. Sci. Instrum., 70(2): 1313-1317 (1999).
Shen, Z. et al., "Microfabrication of Miniaturized PZT/SiO2 Piezoelectric Microcantilever for Rapid, Direct, In-situ Biosensing", MRS Fall Meeting, Boston: 1-23 (2005).
Shen, Z. et al., "Self-exciting, self-sensing PbZr0.53Ti0.47O3/SiO2 piezoelectric microcantilevers with femtogram/Hertz sensitivity", Appl. Phys. Lett., 89: 023506-1-023506-3 (2006).
Shih, W. et al., "Simultaneous liquid viscosity and density determination with piezoelectric unimorph cantilevers", J. Appl. Phys., 89(2): 1497-1505 (2001).
Shih, W. et al., "Ultrasensitive Pathogen Quantification in Drinking Water Using Highly Piezoelectric Microcantilevers", Amer. Chem. Soc., Chapter 23, 179-185 (2005).
Shih, W. et al., "Nanosensors for Environmental Applications", Nanotechnologies for the Life Sciences, 5: 271-293 (2005).

Straub, V. et al., "Contrast Agent-Enhanced Magnetic Resonance Imaging of Skeletal Muscle Damage in Animal Models of Muscular Dystrophy", Magn. Reson. Med., 44: 655-659 (2000).
Thompson, W. R. et al., "Hydrolysis and Condensation of Self-Assembled Monolayers of (3-Mercaptopropyl) trimethoxysilane on Ag and Au Surfaces", Langmuir, 13: 2291-2302 (1997).
Thundat, T. et al., "Detection of mercury vapor using resonating microcantilevers", Appl. Phys. Lett., 66(13): 1695-1697 (1995).
Tslonsky, M. et al., "Sol-Gel-Derived Ceramic-Carbon Composite Electrodes: Introduction and Scope of Applications", Anal. Chem., 66: 1747-1753 (1994).
Tu, Y. L. et al., "A study of the effects of process variables on the properties of PZT films produced by a single-layer sol-gel technique", J. Mater. Sci., 30: 2507-2516 (1995).
Udayakumar, K. R. et al., "Thickness-dependent electrical characteristics of lead zirconate titanate thin films", J. Appl. Phys., 77(8): 3981-3986 (1995).
Wang, Q.M. et al., "Nonlinear piezoelectric behavior of ceramic bending mode actuators under strong electric fields", J. Appl. Phys., 86(6): 3352-3360 (1999).
Wang, Y. et al., "Tactile Mapping of Palpable Abnormalities for Breast Cancer Diagnosis" (1999).
Ward, M. D. et al., "In Situ Interfacial Mass Detection with Piezoelectric Transducers", Science, 249: 1000-1007 (1990).
Wellman, P. S. et al., "Breast Tissue Stiffness in Compression is Correlated to Histological Diagnosis", http://biorobotics.harvard.edu/pubs/mechprops: 1-15 (1999).
Wellman, P. S. et al., "Tactile Imaging of Breast Masses", Arch. Surg., 136: 204-208 (2001).
Wellman, P. S. et al., "Tactile Imaging: A Method for Documenting Breast Lumps", Proceedings of the First Joint BMES/EMBS Conference, Atlanta, Oct. 13-16, 1999, p. 1131.
Weng, L. et al., "Effect of acetylacetone on the preparation of PZT materials in sol/gel processing", Mater. Sci. Engin., B96: 307-312 (2002).
Wilson L S et al., "Elastography—the movement begins", Phys. Med. Biol., 45: 1409-1421 (2000).
Wilson, L., et al., "Pezoelectric-excited millimeter-sized cantilever (PEMC) sensor provides viscosity and density measurements," Submitted to Review of Scientific Instruments, 1-26, (2000).
Yi, J. W. et al., "Effect of length, width, and mode on the mass detection sensitivity of piezoelectric unimorph cantilevers", J. Appl. Phys., 91(3): 1680-1686 (2002).
Yi, J. W. et al., "In situ cell detection using piezoelectric lead zirconate titanate-stainless steel cantilevers", J. Appl. Phys., 93(1): 619-625 (2003).
Zhao, Q. et al., "Array adsorbent-coated lead zirconate titanate (PZT)/stainless steel cantilevers for dimethyl methylphosphonate (DMMP) detection", Sensors and Actuators, B117(1): 74-79 (2006). Abstract Only.
Zhou, J. et al., "Zeolite-modified microcantilever gas sensor for indoor air quality control," Sensors and Actuators B, (Oct. 1, 2003), 94(3), 337-342.
Zhu, D.M. et al., "Thermal conductivity and electromechanical property of single-crystal lead magnesium niobate titanate", Appi. Phys. Lett., 75(24): 3868-3870 (1999).
Data of Commercially Available Product, EDO Corporation: 1-8 (1999).
Data of Commercially Available Product, APC International, Ltd.: 1-2 (2005).
Campbell, GA, et al., "Use of Piezoelectric-Excited millimeter Sized Cantilever Sensors to Measure Albumin Interaction with Self-Assembled Monolayers of Alkanethiols Having Different Functional Headgroups," Anal. Chem. 78, 2328-2334 (2006).
Campbell, G.A., et al., "Method of measuring *Bacillus anthracis* spores in the Presence of copious amounts of *Bacillus thurigiensis* and *Bacillus cereus*," Anal. Chem. 79, 1145-1152 (2007).
Campbell, G.A., et al., "PEMC sensor's mass change sensitivity is 20 pg/Hz under liquid immersion," Biosensors and Bioelectronics, 22, 35-41 (2006).
Campbell, G.A., et al., "Detection of *Bacillus anthracis* spores and a model protein usings PEMC sensors in a flow cell at 1 mL/min," Biosensors and Bioelectronics, 22, 78-85 (2006).

(56) References Cited

OTHER PUBLICATIONS

Campbell, G.A., et al., "Detection of airborne *Bacillus anthracis* spores by an integrated system of an air sampler and a cantilever immunosensor," Sensors and Actuators B 127, 376-382 (2007).

Maraldo, et al., "Method for Label-Free Detection of Femtogram Quantities of Biologics in Flowing Liquid Samples," Anal. Chem. 79, 2762-2770 (2007).

Maraldo, et al., "Detection and confirmation of staphylococcal enterotoxin B in apple juice and milk using piezoelectric-excited millimeter-sized cantilever sensors at 2.5 fg/mL," Anal Chem. 79, 7636-7643 (2007).

Maraldo, et al., "Method for Quantification of a Prostate Cancer Biomarker in Urine without Sample Preparation," Anal. Chem. 79, 7683-7690 (2007).

Maraldo, et al., "10-Minute assay for detecting *Escherichia coli* O157:H7 in ground beef samples using piezoelectric-excited millimeter-size cantilever sensors," Journal of Food Protection, vol. 70, No. 7, 1670-1877 (2007).

Maraldo, et al., "Preapration-Free Method for Detecting *Escherichia coli* O157:H7 in the Presence of Spinach, Spring Lettuce Mix, and Ground Beef Particulates," Journal of Food Protection, vol. 70, No. 11, 2651-2855 (2007).

Rijal, et al., "PEMC-based method of measuring DNA hybridization at femtomolar concentration directly in human serum and in the presence of copious noncomplementary strands," Anal. Chem., 79, 7392-7400 (2007).

Rijal, et al., "Method for measuring the Self-Assembly of Alkanethiols on Gold at Femtomolar Concentrations," Langmuir, 23, 6856-6863 (2007).

Wilson, et al., "Viscosity and density values from excitation level response of piezoelectric-excited cantilever sensors," Sensors and Actuators A 138, 44-51 (2007).

Gu, et al., "Single-Calcination Synthesis of Pyrochlore-Free 0.9Pb (Mg1/3Nb2/3)O3-0.1PbTiO3 and Pb(Mg1/3Nb2/3) O3 Ceramics using a Coating Method," J. Am. Ceram. Soc, 86 [2] 217-21 (2003).

Thaysen, et al., "Cantilever-Based Bio-Chemical Sensor Integrated in a Microliquid Handling System," 401-404 (2001).

Li, et al., Micromachined Biomimetic Sensor Using a Modular Artificial Hair Cells, pp. 1-3 (2000).

Thaysen, "Label free Detection, BioMEMs Materials and Fabrication Methods," Track 2, 3:00pm, pp. 1-3, Sep. 7, 2002.

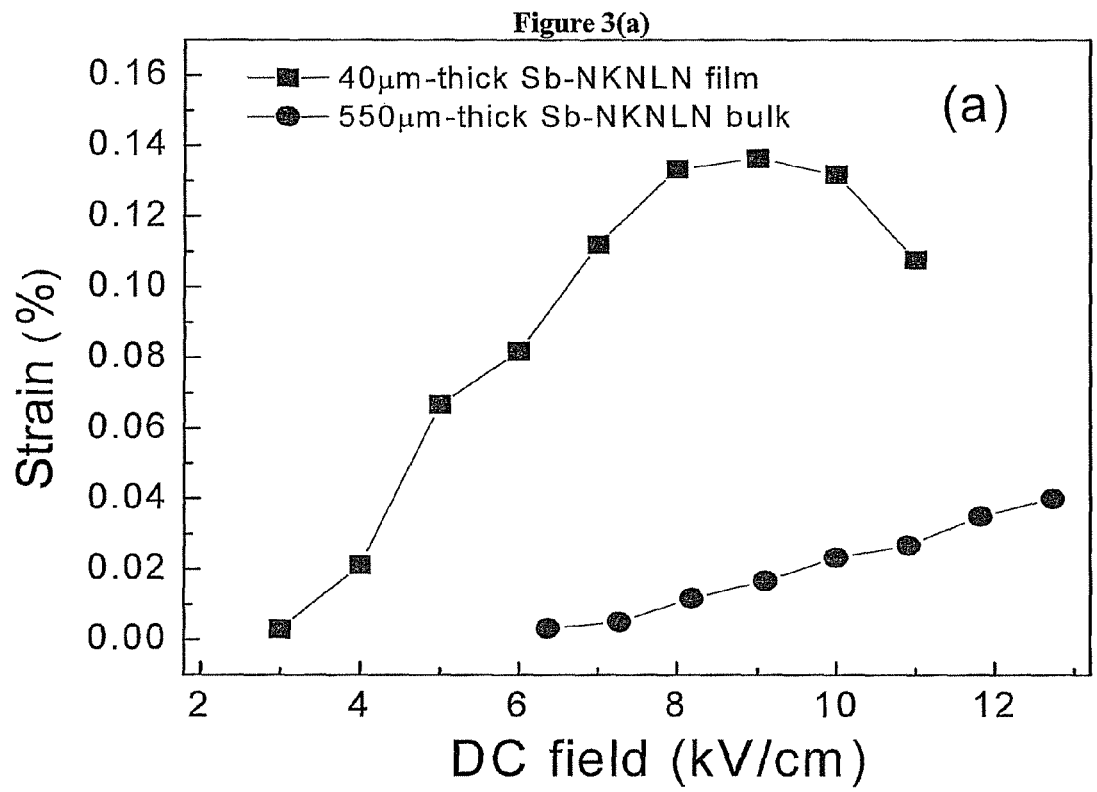
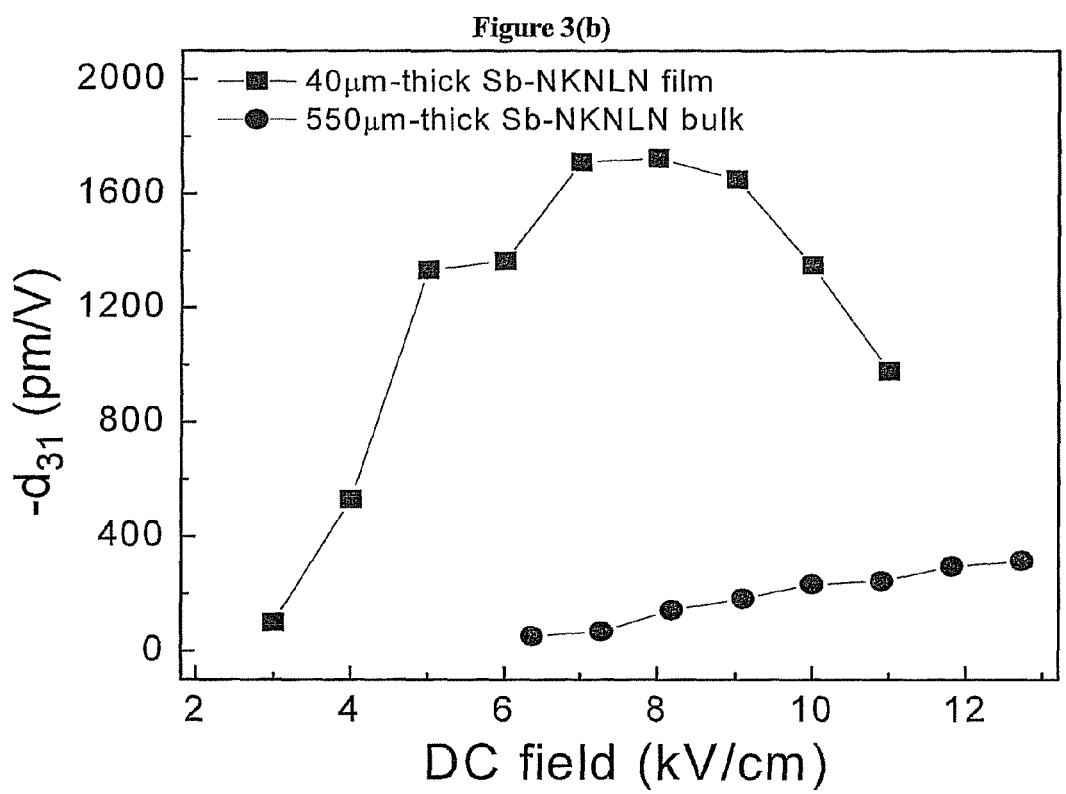

000# LEAD-FREE PIEZOELECTRIC CERAMIC FILMS AND A METHOD FOR MAKING THEREOF

STATEMENT OF GOVERNMENT INTEREST

This invention was made with Government support under Contract No. R01 EB000720 awarded by the National Institutes of Health. The Government has certain rights in the invention.

BACKGROUND OF THE INVENTION

1. Field of the Invention

This invention relates to lead-free piezoelectric ceramic films and a method of making them. Specifically, the invention may be particularly beneficial for use in microelectronic devices such as energy harvesting devices and sensor technologies.

2. Description of the Related Technology

Due to their lead content, current lead based piezoelectric materials and devices are highly toxic. Alternative lead-free piezoelectric materials, however, typically have inadequately low piezoelectric coefficients and thus require complex and expensive methods to provide enhanced piezoelectric activity in order to make them useful. Generally, such methods involve one or more of: texturing the material to align the grains, seeding of plate-like seeds within the green bodies or complex sintering schemes.

Among the lead-free piezoelectric materials, sodium potassium niobate [$(Na_{0.5}K_{0.5})NbO_3$, NKN] offers a high Curie temperature ($T_c \cong 420°$ C.) and a relatively high piezoelectric coefficient ($d_{33}$=80-160 pC/N, $-d_{31}$=32-49 pC/N) (See R. E. Jaeger and L. Egerton, "Hot-Pressing of Potassium-Sodium Niobates," *J. Am. Ceram. Soc.* 45, 209 (1962); H. Birol, D. Damjanovic and N. Setter, "Preparation and Characterization of $(K_{0.5}Na_{0.5})NbO_3$ Ceramics", *J. Eur. Ceram. Soc.* 26, 861 (2006)). To further increase the piezoelectric coefficient, scientists have experimented with various methods for processing solid solutions of NKN with a tetragonal phase-inducing component such as $LiNbO_3$ (LN) and $LiTaO_3$ (LT). By cold isostatic pressing (CIP) this mixture before sintering, the $d_{33}$ coefficient may be increased to about 200 pC/N at the morphotropic phase boundary (MPB) (See Y. Guo, et al., "Phase Transitional Behavior and Piezoelectric Properties of $(Na_{0.5}K_{0.5})NbO_3$—$LiNbO_3$ Ceramics," *Appl. Phys. Lett.*, 85, 4121 (2004); Y. Guo, et al., "$(Na_{0.5}K_{0.5})NbO_3$—$LiTaO_3$ Lead-free Piezoelectric Ceramics," *Mater. Lett.*, 59, 241 (2005)) Mixing NKN, LN, LT and antimony and using a texturing technique, the piezoelectric coefficient may further be increased, wherein $d_{33}$=416 pC/N and $-d_{31}$=152 pC/N (See Y. Saito, H., et al., "Lead-free Piezoceramics," *Nature*, 432, 84 (2004)). To date, 416 pC/N is the best $d_{33}$ coefficient of all lead-free piezoelectric ceramics, which is comparable with the $d_{33}$ coefficient of dominant lead-based piezoelectric materials such as lead zirconate titanate (PZT). However, the methods required to obtain these desirable piezoelectric coefficients are too complex and expensive and consequentially, not suitable for commercialization.

Therefore, there exists a need to develop alternative lead-free piezoelectric materials, more specifically free standing lead-free piezoelectric films having enhanced piezoelectric coefficients.

SUMMARY OF THE INVENTION

The invention is directed to a lead-free piezoelectric material having enhanced piezoelectric properties and a method for making it.

In one aspect, the invention is a method for making a lead-free piezoelectric material by formulating a novel precursor from lead-free compounds, producing a precursor-coated lead-free powder mixture and milling and sintering said powder mixture.

In another aspect, the invention is directed to a material having free-standing film geometry, wherein said film is substantially lead-free and wherein said film has a piezoelectric coefficient $-d_{31}$ of at least about 1600 pm/V.

In a third aspect, the invention is directed to a piezoelectric microcantilever sensor comprising a non-piezoelectric layer, a lead-free piezoelectric layer, at least one conducting element and, optionally, a receptor capable of binding a molecule or compound, wherein the lead-free piezoelectric layer has a piezoelectric coefficient $-d_{31}$ of at least about 1600 pm/V.

BRIEF DESCRIPTION OF THE DRAWINGS

FIG. 2(*b*) depicts a 3.5 in by 7.5 in portable PEMS sensor capable of working with 8 sensors and powered by a 9-V battery.

FIG. 3(*a*) shows a graph of strain as a function of electric field for Sb—NKNLN free-standing film and bulk Sb—NKNLN.

FIG. 3(*b*) shows a graph of dielectric coefficient $-d_{31}$ as a function of the applied electric field for Sb—NKNLN free-standing film and bulk Sb—NKNLN.

FIG. 6(*b*) is a graph of dielectric constant $-d_{31}$ of bulk Sb—NKNLN as a function of the applied electric field.

FIG. 7(*b*) is a graph of in-situ XRD peaks of tetragonal (002) and (200) for the unpoled bulk Sb—NKNLN.

FIG. 8(*b*) is a graph of in-situ XRD peaks of tetragonal (002) and (200) of the poled bulk Sb—NKNLN when the external electric field was applied along the poling direction.

FIG. 9(*b*) is a graph of in-situ XRD peaks of tetragonal (002) and (200) of the poled bulk Sb—NKNLN when the external electric field was applied in the direction opposite to the poling direction.

DETAILED DESCRIPTION OF THE PREFERRED EMBODIMENTS

Figure 1:
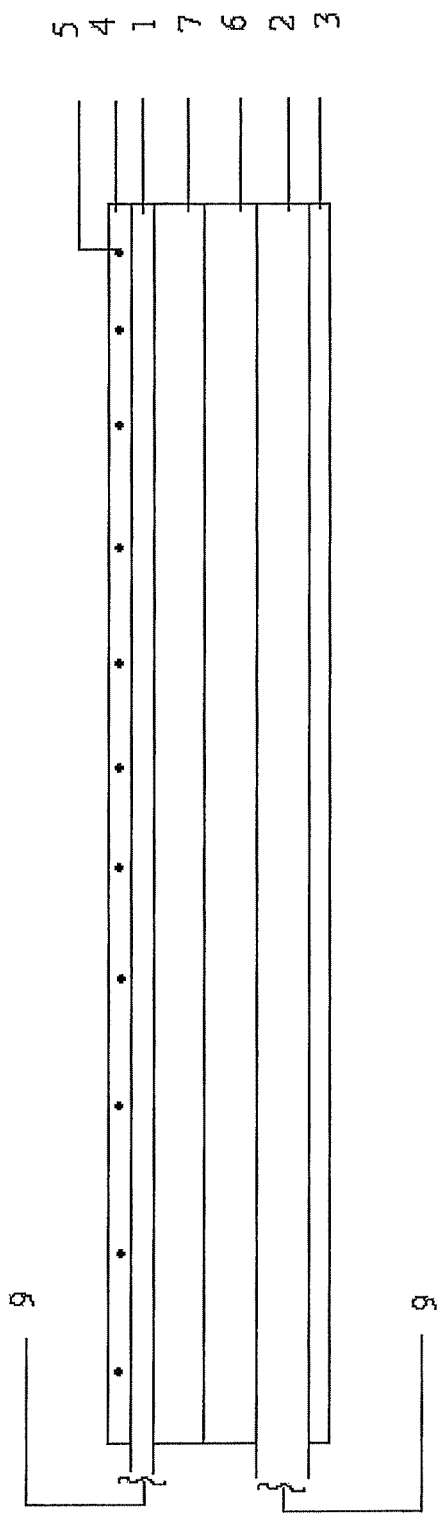
FIG. 1 is a cross section of one embodiment of a piezoelectric microcantilever in which the lead-free piezoelectric material can be employed in accordance with the present invention.

The present invention is directed to free standing lead-free piezoelectric films having enhanced piezoelectric coefficients and a method for making them. The ability of the lead-free piezoelectric materials to retain in-plane polarization even after poling and to increase the population of domains that can be switched by an applied electric field controls their piezoelectric properties.

In one aspect, the present invention provides a novel precursor coating technique for making free standing lead-free piezoelectric films having superior piezoelectric properties. The precursor may be fabricated from lead-free powders, which may be prepared by coating and subsequently processed using traditional tape-casting techniques, such as that disclosed in Huidong Li, Wan. Y. Shih, and Wei-Heng. Shih, "Effect of Antimony Concentration on the Crystalline Structure, Dielectric, and Piezoelectric Properties of (Na0.5K0.5) 0.945Li0.055Nb1−xSbxO3 Solid Solutions," vol. 90, no. 10 (Aug. 2, 2007), which is hereby incorporated by reference in its entirety. In an exemplary embodiment, the tape casting process may involve creating a slurry, which may include the lead-free powder, dopants, organic solvents, binders, plasticizers and deflocculants, and combinations thereof; filtering the slurry to remove undesirable or foreign particles; de-airing the slurry; and casting the slurry by using a doctor blade regulate the formation of a thin film layer, commonly known as green tape.

The precursor may be fabricated by dissolving lead-free compounds in a liquid and adding a dopant to form a precursor suspension. The precursor suspension may be doped with piezoelectric property-enhancing dopants, such as $Sb_2O_5$ particles; any Sb, Sr, Ba, Bi, V containing precursors, compound or particle; or mixtures thereof, to create a precursor suspension that will result in sintered bodies with enhanced piezoelectric properties. Preferably, the precursor suspension is doped with a compound to such that the resultant sintered bodies contain about 3% to about 6% Sb, more preferably about 4% to about 6% Sb. Optionally, the precursor may be doped with any additional desirable dopants, such as particles or precursors that would enhance the piezoelectric, material or mechanical properties of the resultant material. In an exemplary embodiment, lead free compounds $NaNO_3$ (Alfa Aesar, 99%) and $KNO_3$ (Alfa Aesar, 99%) are dissolved in ethylene glycol at about 90° C. Li 2, 4-pentanedionate (Alfa Aesar, 98%) is then added to produce a clear solution, to which $Nb_2O_5$ particles (Alfa Aesar, 99.9%) may be added to form a precursor suspension. In another exemplary embodiment, the precursor suspension is formulated from lead-free compounds, niobium oxide, titanium oxide particles and/or mixtures thereof. The precursor suspension may then be subsequently ultrasonicated to break up the formation of any agglomerates and then dried to obtain the precursor-coated lead-free powder mixture. This novel coated precursor powder mixture facilitates sintering and enables the production of free standing films, which can be easily incorporated into microelectronic devices.

The coated precursor powder mixture may be calcined and ball milled using any suitable method. The coated precursor powder may subsequently be mixed with dispersing resins, plasticizers, other desirable additives and/or mixtures thereof prior to being subject to further ball-milling, de-airing, casting, i.e. tape-casting, and sintering using any suitable method. In a preferred embodiment, sintering may be carried out in crucibles sealed by packing powder having the same composition as the resulting lead-free piezoelectric film. This fabrication method is robust and may be readily applied to the formation of any lead-free piezoelectric material, such as $(Na_{0.5}K_{0.5})_{0.9451}Li_{10.055}Nb_{0.96}Sb_{0.04}O_3$ (hereinafter "Sb—NKNLN"), $Sb—(Na_{0.5}K_{0.5})NbO_3—LiTaO_3$ (hereinafter "Sb—NKNLT"), $Sr—(Na_{0.5}K_{0.5})NbO_3—LiTaO_3$ (Sr—NKNLN), $Sr—Na_{0.5}K_{0.5}NbO_3—LiTaO_3$ (Sr—NKNLT), $SbSr—(Na_{0.5}K_{0.5})NbO_3—LiTaO_3$ (SrSb—NKNLN), $SrSb—Na_{0.5}K_{0.5}NbO_3—LiTaO_3$ (SbSr—NKNLT), solid solutions with $(Bi_{0.5}K_{0.5})TiO_3$, $(Bi_{0.5}Na_{0.5})TiO_3$, $Ba(Zr_xTi_{1-x})O_3$, $BaTiO_3$ (hereinafter "BT"), $(Bi_{1/2}K_{1/2})TiO_3$ (hereinafter "BKT"), $(Bi_{1/2}Na_{1/2})TiO_3$ (hereinafter "BNT"), $Ba(Zr_xTi_{1-x})O_3$ (hereinafter "BZT"), $Bi(Zn_{1/2}Ti_{1/2})O_3$ (hereinafter "BiZT"), $(Na_xK_{1-x})NbO_3$ (hereinafter "NKN"), $BiScO_3—PbTiO_3BaTiO_3—(Bi_{1/2}K_{1/2})TiO_3$ (hereinafter "BKBT"), $(Bi_{1/2}Na_{1/2})TiO_3—(Bi_{1/2}K_{1/2})TiO_3$ (hereinafter "BNKT"), $(Bi_{1/2}Na_{1/2})TiO_3—BaTiO_3$ (hereinafter "BNBT"), $(Bi_{1/2}Na_{1/2})TiO_3—Ba(Zr_xTi_{1-x})O_3$ (hereinafter "BNBZT") and $(Bi_{1/2}Na_{1/2})TiO_3—BaTiO_3—(Bi_{1/2}K_{1/2})TiO_3$ (hereinafter "BNBK").

The resulting lead-free piezoelectric material may be fabricated in any form, preferably having free standing film geometry. The lead-free piezoelectric material may have enhanced piezoelectric characteristics such as high piezoelectric coefficients. Typically, the piezoelectric performance of a polycrystalline piezoelectric material excited by an applied electric field is mainly dictated by domain wall motion, i.e. domain switching, in the material. Whereas the switching ability of ferroelectric domains is severely inhibited in silicon-substrate-based thin films, the free standing film geometry of the lead-free piezoelectric material of the present invention has enhanced piezoelectric properties because it eliminates the clamping effect caused by the substrate, thereby enabling the domain wall to switch much more readily under an electric field. Also, the strong depolarization field induced by the film geometry causes the ferroelectric domains of the lead-free piezoelectric material to lie down in the planar direction, thereby facilitating domain switching upon application of a sufficiently large electric field. Further, the small numbers of grains, i.e. large grain size, in the thickness direction gives significantly less grain boundary and facilitates penetration of an applied electric field, both of which promote domain wall motion.

In an exemplary embodiment, the free standing lead-free piezoelectric film has a large piezoelectric coefficient $-d_{31}$ of about 200 to about 2000 pm/V, more preferably about 1500 pm/V to about 1800 pm/V and most preferably about at least 1600 pm/V to about 1700 pm/V at an applied electric field of about 8 kV/cm. In an exemplary embodiment, the lead-free piezoelectric free standing films has large piezoelectric coefficients $-d_{31}$ and/or $d_{33}$ at 8 kV/cm and may be fabricated to have a thickness ranging on the level of a few microns to hundreds of microns. Preferably, the thickness of the film is about 4 μm to about 100 μm.

The method of the present invention is advantageous in that it is capable of producing a non-toxic lead-free piezoelectric material having a large piezoelectric coefficient using a simple and inexpensive process which would enable manufacturing for mass production. The method is novel in that it only requires coating a precursor and subsequent sintering of the precursor powder compact.

The non-toxic lead-free piezoelectric material of the present invention has numerous applications. Specifically, since it may be easily incorporated into any microelectronic devices such as micro-electro-mechanical systems (MEMS) devices, it may be particularly useful in the microelectronics industry. If driven by an electric field, the material may be stacked to multiply the output energy. The large piezoelectric coefficient and high sensitivity of the material is also beneficial for sensor technologies as well as energy harvesting applications. It is envisioned that the lead-free piezoelectric film of the present invention may be used to as the piezoelectric layers of a mechanical energy harvesting device or a microelectronic sensor. Furthermore, the non-toxic lead-free piezoelectric material of the present invention may be used as a substitute for any piezoelectric material in any application or in any piezoelectric commercial product. It is believed that the non-toxic lead-free piezoelectric material will facilitate the compliance of piezoelectric commercial products with health and safety regulations, such as RoHS.

In an exemplary application, the lead-free piezoelectric material may be used to fabricate a piezoelectric microcantilever sensor (PEMS). PEMS are biological and chemical sensors that may be used for biological or chemical detection using an electrical sensing means. Receptors may be coated on the surface of the PEMS to bind molecules of interest. Binding of the target molecules to immobilized receptors on the PEMS surface shifts the mechanical resonance frequency of the device. By monitoring resonance frequency shifts, the PEMS is capable of rapid, label-free, in situ quantitative detection of organic compounds or molecules including pathogens, antigens and proteins in a small volume solution (e.g. 100 µl) or in a cell culture using simple all-electrical measurements. In a preferred embodiment, the PEMS is capable of electric actuation and detection and may also be constructed as an array for simultaneous monitoring of multiple target compounds or molecules.

PEMS having a lead-free piezoelectric layer may be particularly promising for the detection of bioterrorism agents. Antibody receptors specific to at least one bioterrorism agent may be bound to an electrode and used to detect the presence of a bioterrorism antigen. In addition to identifying the existence of a bioterrorism agent, it may also be used to quantify the concentration of the agent.

Additionally, PEMS having a lead-free piezoelectric layer may be useful in the health sciences as a diagnostic instrument. It may be used as a means for early detection of cancers and other diseases. It may also be used to monitor the progress of the disease throughout treatment. The PEMS may be incorporated in a portable device and used as a noninvasive means for testing blood and other bodily fluids for various pathogens, infectious agents and other markers indicative of disease.

Specifically, it is envisioned that the lead-free piezoelectric layer may be incorporated in a PEMS that may be used for in-vivo tissue elasticity imaging applications including cancer detection, such as breast cancer, detection, location and differentiation, as well as skin elasticity imaging.

Such PEMS may also be particularly applicable for the food science and food manufacturing industry. PEMS may be used as a diagnostic instrument for detecting pathogens or other disease agents present in food supplies and prepared or processed foods. Additionally, it may also be useful in manufacturing plants and food service industries as a means of intermittently checking food products during different phases of food preparations thereby preventing contamination and the spread of bacterial or viral diseases such as *salmonella* and *E. coli*.

FIG. 1 shows the basic structure of an exemplary PEMS. FIG. 1 shows a first conductive element 1 and a second conductive element 2 (bottom electrode), electrical insulating layer 3, receptor immobilization layer 4, receptors 5, at least one non-piezoelectric layer 6, and at least one piezoelectric layer 7. The PEMS shown in FIG. 1 may also include electrical leads 9.

Conductive elements 1, 2 may be any element capable of conducting an electrical signal from the piezoelectric layer to a device for detecting that signal. In a preferred embodiment, conductive elements 1 and 2 are electrodes which may be constructed from any conductive material. Preferably, the first electrode 1 is constructed from Au/Cr or Pt/Ti and subsequently patterned in several regions. The second electrode 2 is preferably constructed from Pt/$TiO_2$ on $SiO_2$ or Pt/Ti on a metal substrate or non-piezoelectric layer and subsequently patterned as well.

In order to maintain functionality in solution by preventing conduction, it may be useful to electrically separate or buffer conductive element 1 and second conductive element 2. Conductive element 1 is patterned slightly smaller than the piezoelectric layer 7 to ensure complete insulation of the edges and corners thereof. Any electrically insulating layer 3 may be used as a coating to achieve electrical separation or buffering.

In one embodiment, insulating layer 3 may comprise a 1.5 µm thick parylene (poly-para-xylylene) coating deposited on an electrode by chemical vapor deposition. When placed in static and 1 ml/min flow rate of PBS solution, a parylene insulating layer 3 essentially prevents background resonance frequency shifts greater than 30 Hz and 60 Hz, respectively, over a period of 30 minutes. As a result, insulating layer 3 enables complete submersion of the microcantilever for in situ or in-solution detection while maintaining a Q value (quality value) greater than 35. For the purposes of this patent application, Q value is defined as the ratio of the resonance frequency to the resonance peak width at half the peak height.

Alternatively, the PEMS may be insulated using self-assembled monolayers with hydrophobic properties, preferably methyltrimethoxysilane (MTMS) or a combination of MTMS with parylene coatings of varying thicknesses, may also be used. When immersed in a PBS solution, an MTMS insulated piezoelectric microcantilever yields strong resonance peak intensities and prevents background resonance frequency shifts greater than 30 Hz over a period of 30 minutes.

Other insulation materials may include $Al_2O_3$, $SiO_2$ and any functional hydrophobic silane, having a hydrophobic group selected from the group consisting of alkyl, phenyl, alkyl halide, alkene, alkyne, and sulfhydryl. In a preferred embodiment, the insulation material is mercaptopropylsilane (MPTS), which can also function to immobilize a receptor on the cantilever.

Receptors 5 may be densely packed and immobilized onto, for example, a bi-functional linker modified sensor surface. Any receptor, such as specially synthesized cavitants, DNA oligonucleotides, proteins, single chain variable fragments (scFvs), enzymes, and antibodies to cells, antigens or pathogens, may be bound to the sensor surface. For example, when trying to detect tumors, monomeric and dimeric anti-tumor scFv molecules, which are composed of variable light and heavy chains of antibody molecule anti-ECD scFV, that react to cancer markers may be bound to the electrodes. Similarly, when trying to detect *Bacillus anthracia* ("BA"), antibodies specific to BA spore surface antigens may be immobilized on the electrodes.

Any means of adhering receptors 5 to the sensor surface may be utilized. In a preferred embodiment, receptors 5 are bound to the electrodes using an immobilization coating 4, such as self assembled monolayers ("SAM"), MPTS and bi-functional linkers. In one embodiment, for purposes of binding scFv, the immobilization coating may be a self assembled monolayer of 3-mercaptoproprionic acid (MPA) on a copper and gold-coated electrode activated with 1-ethyl- 3-(3-dimethylaminopropy)carbodimide hydrochloride (EDC) and 5 mg/ml N-hydroxysulfosuccinimide (NHS).

The PEMS also includes at least one non-piezoelectric layer 6, which may be fabricated from any compatible material, including ceramic, polymeric or metallic materials. Preferably the non-piezoelectric layer 6 is fabricated from silicon dioxide ($SiO_2$), silicon nitride ($Si_3N_4$), any ceramic, metallic, or polymeric layer. A metallic layer such as Cu, tin, Ni, Ti, etc., or any combination is preferred because it can be provided by simple electroplating. For example, a silicon nitride coating on single crystal silicon wafer may be prepared by low press chemical vapor deposition. A low stress silicon dioxide layer may subsequently be deposited on the silicon nitride layer by growing silicon dioxide films using low temperature oxide deposition or plasma enhanced chemical vapor deposition.

Non-piezoelectric layer 6 may be bonded to a shorter piezoelectric layer 7 so that the portion of non-piezoelectric layer 6 extending beyond the end of piezoelectric layer 7 forms a non-piezoelectric tip. Both piezoelectric layer 7 and non-piezoelectric layer 6 may be attached to a clamp. In an alternative embodiment, piezoelectric layer 7 may extend beyond non-piezoelectric layer 6, forming a piezoelectric tip. In order to achieve the best results, one of the piezoelectric 7 and non-piezoelectric layers 6 preferably extends beyond the other to form a tip. A PEMS may also include multiple piezoelectric and non-piezoelectric layers. For example, a non-piezoelectric layer may be placed between two piezoelectric layers or a piezoelectric layer may be placed between two non-piezoelectric layers.

A significant aspect of the microcantilever device is the fabrication of a non-toxic lead-free highly sensitive piezoelectric layer 7, which enables electrical detection and actuation within the cantilever. Piezoelectric layer 7 may be constructed from any non-toxic piezoelectric material, preferably a lead-free piezoelectric material fabricated in accordance with the precursor coating and sintering method, discussed above. The piezoelectric layer may function as a driving element, vibrating element and sensing element. Applying an AC voltage (input) across the piezoelectric layer bends and vibrates the PEMS, which in turn induces a piezoelectric voltage that produces readily detectable changes in the magnitude and phase of the output voltage. The resonance frequency of the PEMS is obtained by monitoring the maximum of the phase shift of the output voltage. This measurement is accomplished all-electrically, i.e., electrical actuation and electrical sensing.

To further increase sensitivity and expedite the detection process, the PEMS may be immersed in a flowing solution for in-solution detection. The PEMS is preferably situated in a flow cell system to enable tailored, rapid and simultaneous detection and quantification of multiple organic compounds or molecules.

Figure 2A:
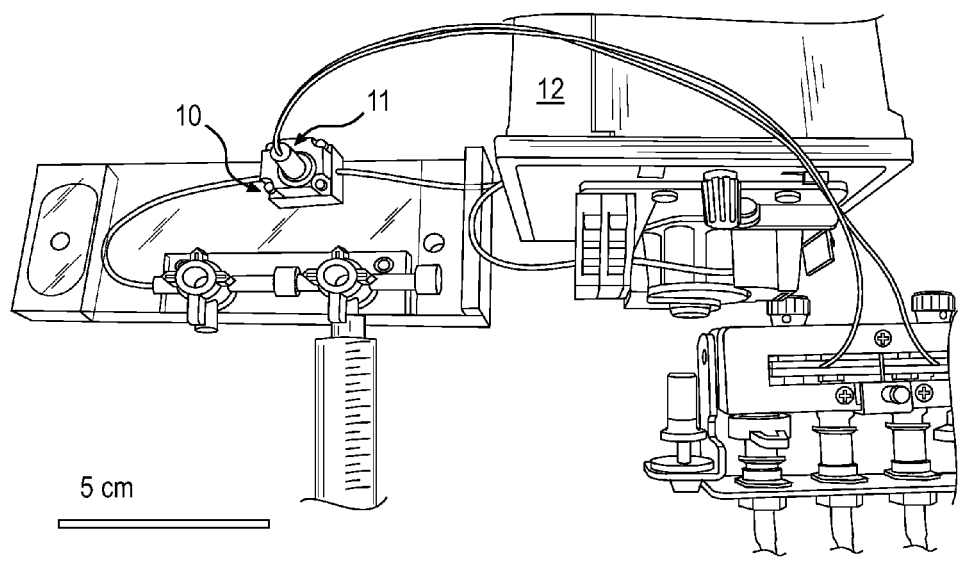
FIG. 2(*a*) depicts a flow cell system which can be used in conjunction with the piezoelectric cantilevers.
Figure 2B:
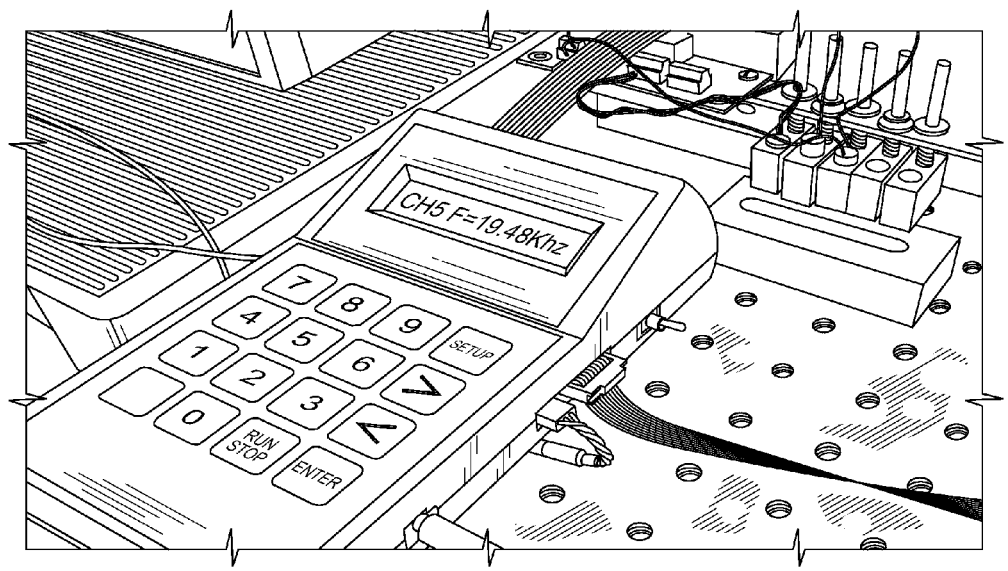

FIG. 2(a) shows a flow cell system 10, with a PEMS holder/measuring unit 11, having a total volume of less than 0.03 ml, pump 12, and a mechanism for controlling temperature and humidity (not shown). The flow cell 10 may attain flow rates of up to 1 ml/min The total volume of the flow cell, number of channels and flow rate may vary depending upon the number of compounds to be measured. The flow cell 10 may cooperate with a portable PEMS unit, shown in FIG. 2(b), which has multiple channels for the simultaneous quantification of multiple receptor specific molecules. The portable PEMS is inexpensive and capable of obtaining quick measurements.

Another means for further enhancing sensitivity is by increasing humidity. The mass change per unit area per percent humidity change of PZT PEMS is estimated to be about $1.2 \times 10^{-11}$ g/Hz/mm²/% humidity. The sensitivity of PMN PEMS by comparison is known to be about three times greater than that of PZT PEMS.

The resultant PEMS are chemically inert, thermally stable and miniaturized to enhance sensitivity. They function by binding target molecules that react to the receptors immobilized on the electrodes. The corresponding change in mass shifts the mechanical resonance frequency of the microcantilever. The PEMS is capable of detecting these shifts in resonance frequency by monitoring the $i^{th}$-mode flexural resonance frequency f which is related to the effective spring constant, $K_e$, and effective mass, $M_e$, of the piezoelectric cantilever at the tip as shown in Equation 2.

$$f_i = \frac{1}{2\pi}\sqrt{K_e/M_e} \qquad \text{(Equation 2)}$$

The binding of a receptor specific molecule to the cantilever surface changes the cantilever mass and the cantilever spring constant. The resonance frequency shift Δf, expressed in Equation 3, $$\Delta f_i = f_i\left(-\frac{\Delta m}{2M_e} + \frac{\Delta k}{2K_e}\right) \qquad \text{(Equation 3)}$$

where Δm and Δk denote the mass change and the effective spring constant, model the functionality of the microcantilever.

These PEMS may be used for various sensing applications such as solid-liquid transition detectors, liquid viscosity and density sensors, mass sensors for in situ and in-water detection. PEMS may generally be used for detection of any molecule or organic compound.

Example 1

In an exemplary embodiment, the method of the present invention may be used to fabricate lead-free Sb—NKNLN free standing films. A precursor solution was first formulated by dissolving $NaNO_3$ (Alfa Aesar, 99%) and $KNO_3$ (Alfa Aesar, 99%) in about 200 ml of ethylene glycol at about 90° C. and subsequently adding lithium-2,4-pentanedionate (Alfa Aesar, 98%) to produce a clear solution. Next, the $Nb_2O_5$ particles (Alfa Aesar, 99.9%) and $Sb_2O_5$ particles (Alfa Aesar, 99.998%) were added to the precursor solution, resulting in a 0.5 M concentration. The suspension was then ultrasonicated for about 5 minutes to break up the $Nb_2O_5$ and $Sb_2O_5$ agglomerates and then dried to obtain the precursor-coated $Nb_2O_5$ and $Sb_2O_5$ lead-free powder mixture.

After calcination at about 850° C. for about 2 hours, the powder was ball-milled for about 24 hours and sieved using #45 and #100 meshes for better packing. The powder was then mixed with a proprietary dispersing resin and ball milled in an alcohol-ketone mixture for about 24 hours. With the remaining resin and a phthalate-based plasticizer, the precursor powder was further ball-milled for about 24 hours, de-aired, cast to the desired thickness, and sintered at about 1100-1120° C. for about 2 hours. Sintering was carried out in alumina crucibles sealed by a packing powder having the same composition as that of the film.

Example 2 and Comparative Example A

A 40-nm-thick lead-free Sb—NKNLN free standing film fabricated in accordance with the method of Example 1, was tested for its piezoelectric properties.

The film was first configured to form a microcantilever sensor and an electric-field was applied to the sensor. The determination of the piezoelectric coefficient $-d_{31}$ of the Sb—NKNLN film was carried out using two different methods: (1) direct measurement, wherein the lateral displacement of the piezoelectric strip was measured under an applied electric field, i.e. the converse piezoelectric effect, and (2) cantilever bending measurement, wherein the tip displacement of a cantilever, consisting of the piezoelectric film bonded to a non-piezoelectric layer such as copper, was measured under an applied electric field. In both measurement methods, a laser displacement meter (Keyence, model LC2450) was used to acquire the displacements. For method (1), both sides of the cantilever were sputtered with Pt electrode. A small piece of 0.002-inch thick titanium foil was attached to the tip of the cantilever as a minor for the laser to focus on. For method (2), one side of the cantilever was sputtered with Pt and the other side was electroplated with copper as a non-piezoelectric layer to induce bending upon the application of electric field. The laser beam was directly focused on the cantilever surface at the tip.

The strain was determined by measuring the lateral displacement of a Sb-doped NKN-LN strip having a thickness of about 40 μm and a Sb-doped NKN-LN bulk bar having a thickness of about 550 μm under an applied electric field. The $-d_{31}$ coefficient values were deduced by dividing the measured strain by the applied electric field.

As shown in FIG. 3, as DC electric field increased the strains and $-d_{31}$ values of both the Sb-doped NKN-LN film and the Sb-doped NKN-LN bulk bar. However, the free standing film showed a much larger strain increase and to a much higher value than the bulk bar, resulting in about 10-fold to 20-fold increase in the $-d_{31}$ value. The Sb—NKNLN bulk materials produced $-d_{31}$ values ranging from −82 to −116 pm/V (See H. Li, et al., "Effect of Antimony Concentration on the Crystalline Structure, Dielectric and Piezoelectric Properties of $(Na_{0.5}K_{0.5})_{0.945}Li_{0.055}Nb_{1-x}Sb_xO_3$ Solid Solutions", *J. Am. Ceram. Soc.*, 90, 3070 (2007); and S. Zhang, et al., "Piezoelectric Properties in Perovskite $0.948(K_{0.5}Na_{0.5})NbO_3$-$0.052LiSbO_3$ lead-free ceramics", *J. App. Phys.*, 100, 104108 (2006)). The determined $-d_{31}$ value induced at a low electrical field of about 6 to about 8 kV/cm agreed with the reported values.

An ESEM photograph of the cross-section of the Sb—NKNLN free-standing film shows that the film is fully dense and that there are only about 10 to about 20 grains across the thickness direction of the film.

Figure 4:
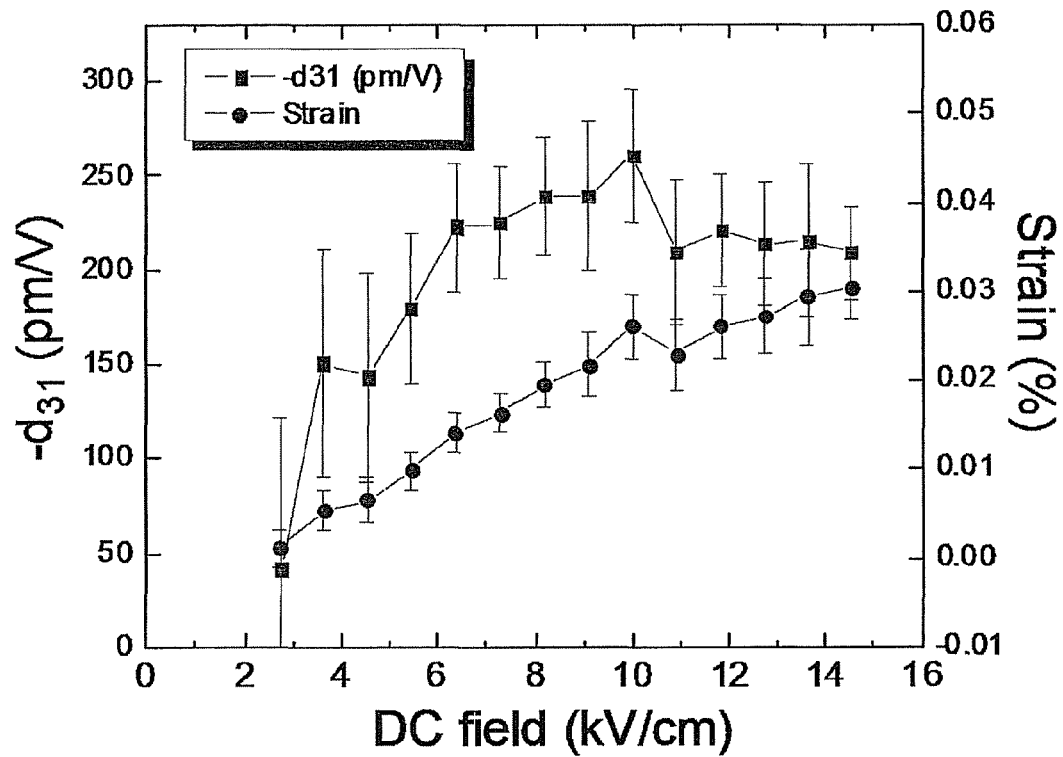
FIG. 4 is a graph of strain and dielectric coefficient $-d_{31}$ of an undoped NKN free-standing strip as functions of an applied electric field.

Direct measurement of $-d_{31}$ was also performed on undoped NKN to verify the electric-field enhancement of the free standing film geometry. FIG. 4 shows the behavior of the lateral strain and the determined $-d_{31}$ value of an undoped NKN free standing strip having a thickness of about 60 μm under an applied electric field. When the electric field was lower than about 3 kV/cm, the lateral displacement of the strip was smaller than the resolution of the laser displacement meter. Thus, no reading was obtained at those fields. At about 3 kV/cm, a determined $-d_{31}$ value of about 41 pm/V was obtained, consistent with the reported $-d_{31}$ value of undoped NKN at an field of about 32 to about 49 pm/V. Similar to the behavior of Sb—NKNLN free standing films, as the electric field increased, the $-d_{31}$ increased and reached a maximum of about 250 pm/V at about 10 kV/cm, which represents about a 5-fold increase compared to the value of the bulk bar.

The $-d_{31}$ value of the Sb—NKNLN film was also measured by bonding the free-standing films to a nonpiezoelectric layer forming a cantilever and performing cantilever bending measurement. The cantilevers used for this measurement was about 3 mm to about 4 mm long and about 0.5 mm to about 0.7 mm wide. One side of the cantilever was incorporated a Pt-electrode and the other side was electroplated with Cu. The thickness of the Sb—NKNLN material in the cantilever was about 40 μm, and the thickness of the Cu nonpiezoelectric layer was about 25 μm. The piezoelectric layer may, in some cases, be denser than the nonpiezoelectric layer.

The laser beam of the laser displacement meter was focused on the tip of the cantilever which was screwed to an optical table. Upon the application of the electric field across the thickness direction of the Sb—NKNLN layer, the cantilever deformed due to the constraint of the copper non-piezoelectric layer resulting in a vertical displacement of the cantilever tip, which was monitored by the displacement meter. The $-d_{31}$ value of the Sb—NKNLN film was then determined using the following equation:

$$d_{31} = \frac{h_{can}t_2}{3VL^2} \cdot \frac{E_1^2 t_1^4 + E_2^2 t_2^4 + 2E_1 t_1 E_2 t_2 (2t_1^2 + 2t_2^2 + 3t_1 t_2)}{E_1 E_2 t_1 (t_1 + t_2)(1 - v)} \quad (1)$$

where $h_{can}$ is the cantilever tip displacement, V is the applied DC voltage, L is the length of the cantilever, $v \approx 0.3$ the Poisson's ratio, $t_1$ and $t_2$ the thicknesses of Cu and Sb—NKNLN, $E_1=130$ GPa and $E_2=82$ GPa the Young's modules of Cu and Sb—NKNLN, respectively.

Figure 5:
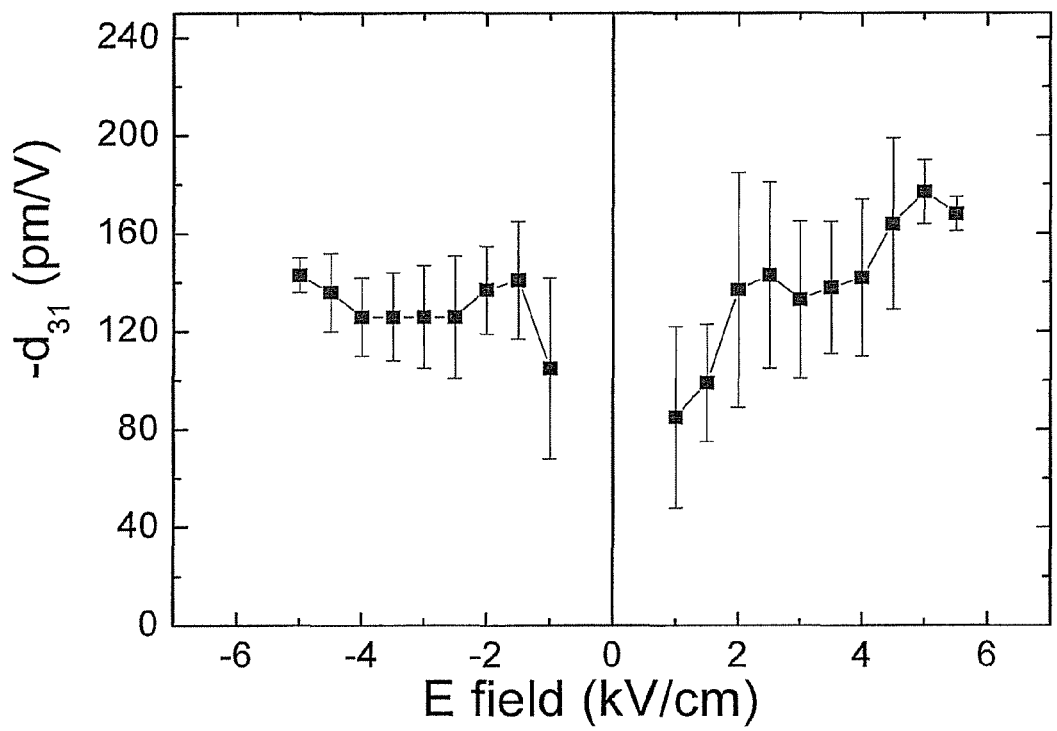
FIG. 5 is a graph of the dielectric constant $-d_{31}$ of Sb—NKNLN film deduced from cantilever bending measurement as a function the applied electric field.

As shown in FIG. 5, the $-d_{31}$ value obtained using the cantilever bending measurement was much smaller than that of the direct measurement from the Sb—NKNLN strip. This was likely due to the presence of the Cu layer. In the direct measurement, the thickness of the Pt electrodes coated on both sides of the Sb—NKNLN film was only in the nanometer magnitude. Because the electroplated Cu layer used in the bending measurement has a similar thickness in comparison to that of the Sb—NKNLN layer, it could have compromised the "free-standing" condition of the Sb—NKNLN film and consequently produced a smaller enhancement of the piezoelectric coefficient. Nevertheless, the $-d_{31}$ value of Sb—NKNLN still showed about a 2-fold increase at a field of about 5 kV/cm.

Example 3 and Comparative Example B

The Sb—NKNLN free standing films of Example 1 were also evaluated for domain switching capabilities.

Domain switching in ferroelectrics may be classified as: 180° domain switching and non-180° switching. Only non-180° domain switching induces strain in the material. Two different approaches were used to determine the ease of the film's non-180° domain switching capabilities, namely: (1) studying the behavior of the dielectric constant of the material under an increasing electric field and (2) studying in-situ XRD patterns of the film under an electric field.

Figure 6A:
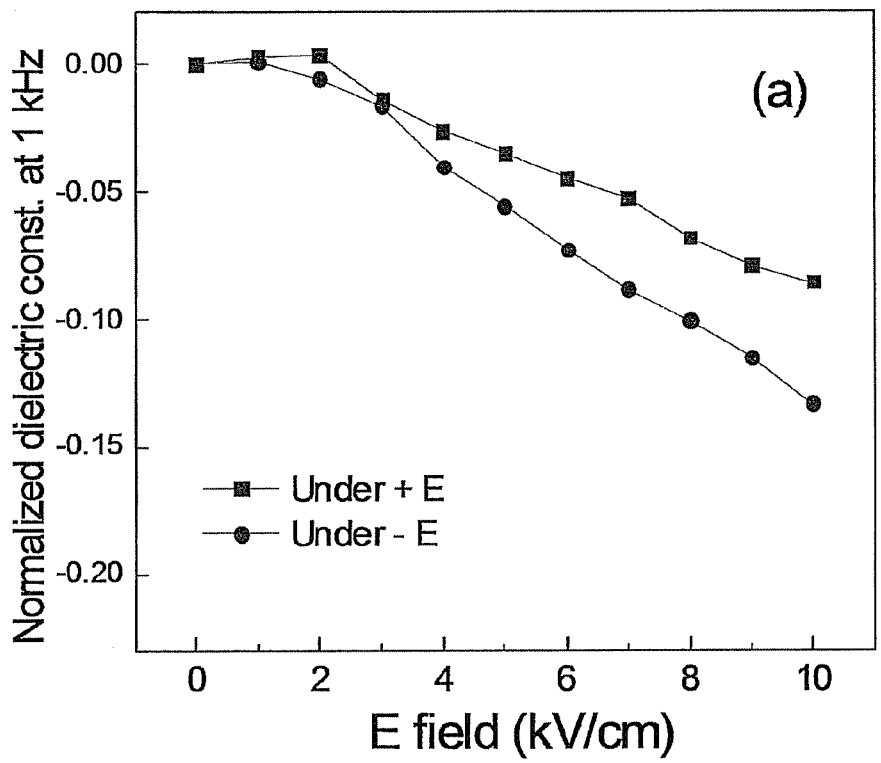
FIG. 6(*a*) is a graph of dielectric constant $-d_{31}$ of the Sb—NKNLN free-standing films as a function of the applied electric field.
Figure 6B:
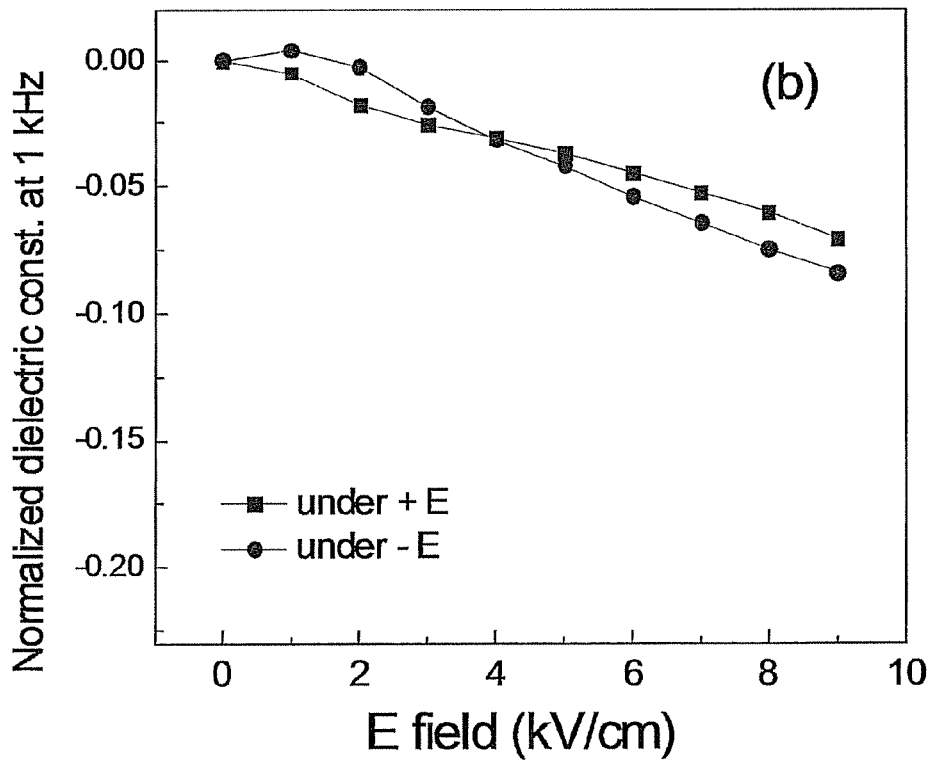

Generally, the tetragonal a-domain has a larger dielectric constant than the tetragonal c-domain Under a sufficiently large electric field, in the free standing ferroelectric film, the dominant a-domains whose polarization directions are along the planar direction, will switch by 90° and become c-domains. As a result, a decrease in the dielectric constant is expected. Therefore, the behavior of the dielectric constant under an external electric field is an indication of the non-180° domain wall motion. FIGS. 6(a)-6(b) shows the normalized dielectric constant of the Sb—NKNLN free standing films and the bulk bar as functions of electric field. The electric field was applied along the poling direction of the sample or opposite to the poling direction.

As shown in FIG. 6(b), the behavior of the bulk bar remained fairly uniform. An 8% decrease in the dielectric constant was observed in both positive and negative electric field directions at a 10 kV/cm field. By contrast, the free standing film showed asymmetric behavior. When the electric field direction is the same as that of the poling direction, the film exhibited a similar degree of decline in the dielectric constant as that of the bulk bar sample. When the field is opposite to the poling direction, the dielectric constant showed a greater decline of over about 13% at 10 kV/cm, indicating that the free standing films enable easier non-180° domain switching.

Non-180° domain wall motion was also determined by measuring the change of the XRD patterns of the material under an applied electric field. The integrated intensity of the XRD peaks corresponds to the populations of a-domains and c domains (X. Li, W. Y. Shih, J. S. Vartuli, D. L. Milius, I. A. Aksay, and W.-H. Shih, "Effect of Transverse Tensile Stress on Electric-Field-Induced Domain Reorientation in Soft PZT: In Situ XRD Study", *J. Am. Ceram. Soc.* 85 (4), 844 (2002)).

Figure 7A:
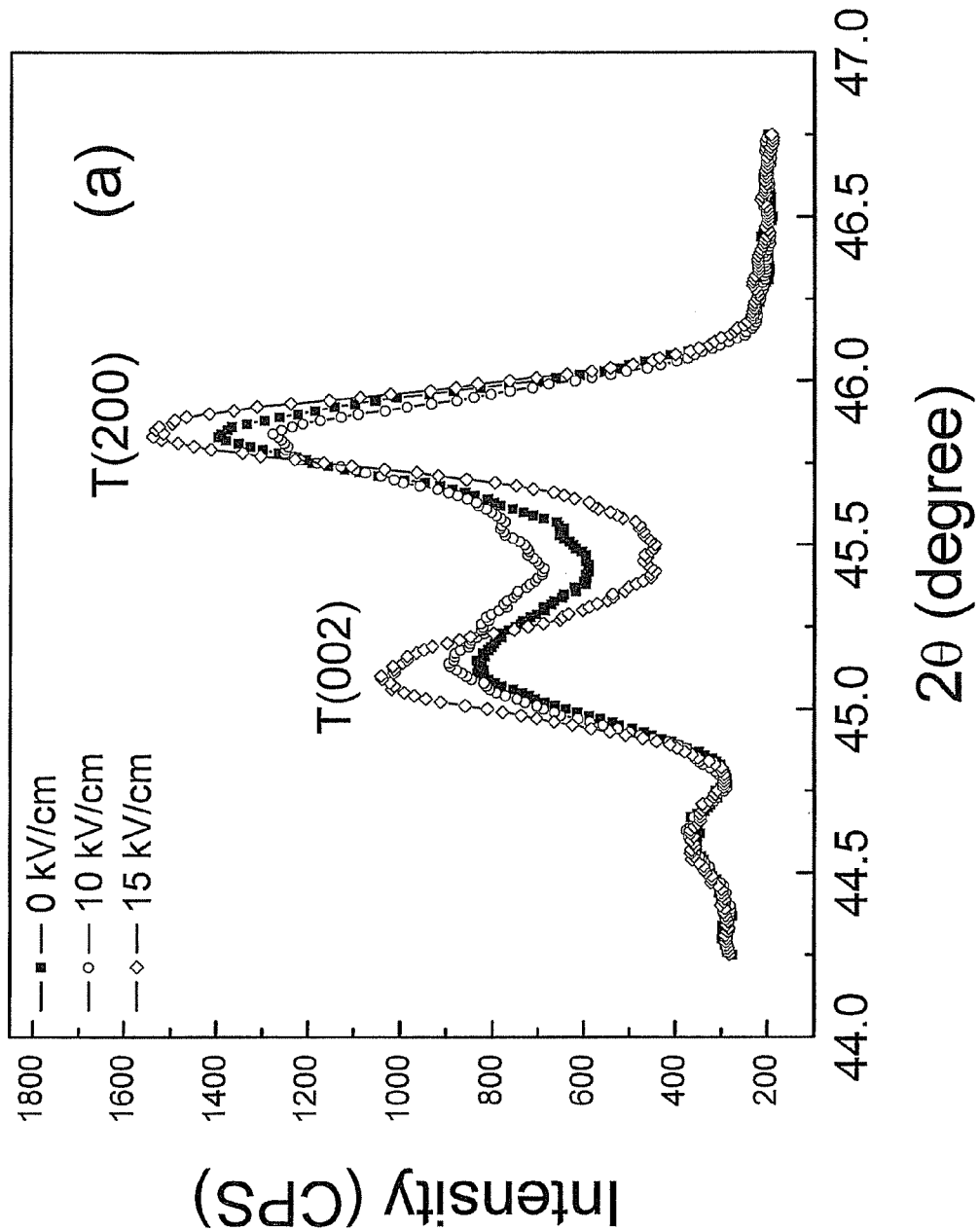
FIG. 7(*a*) is a graph of in-situ XRD peaks of tetragonal (002) and (200) for the unpoled Sb—NKNLN free-standing film.
Figure 7B:
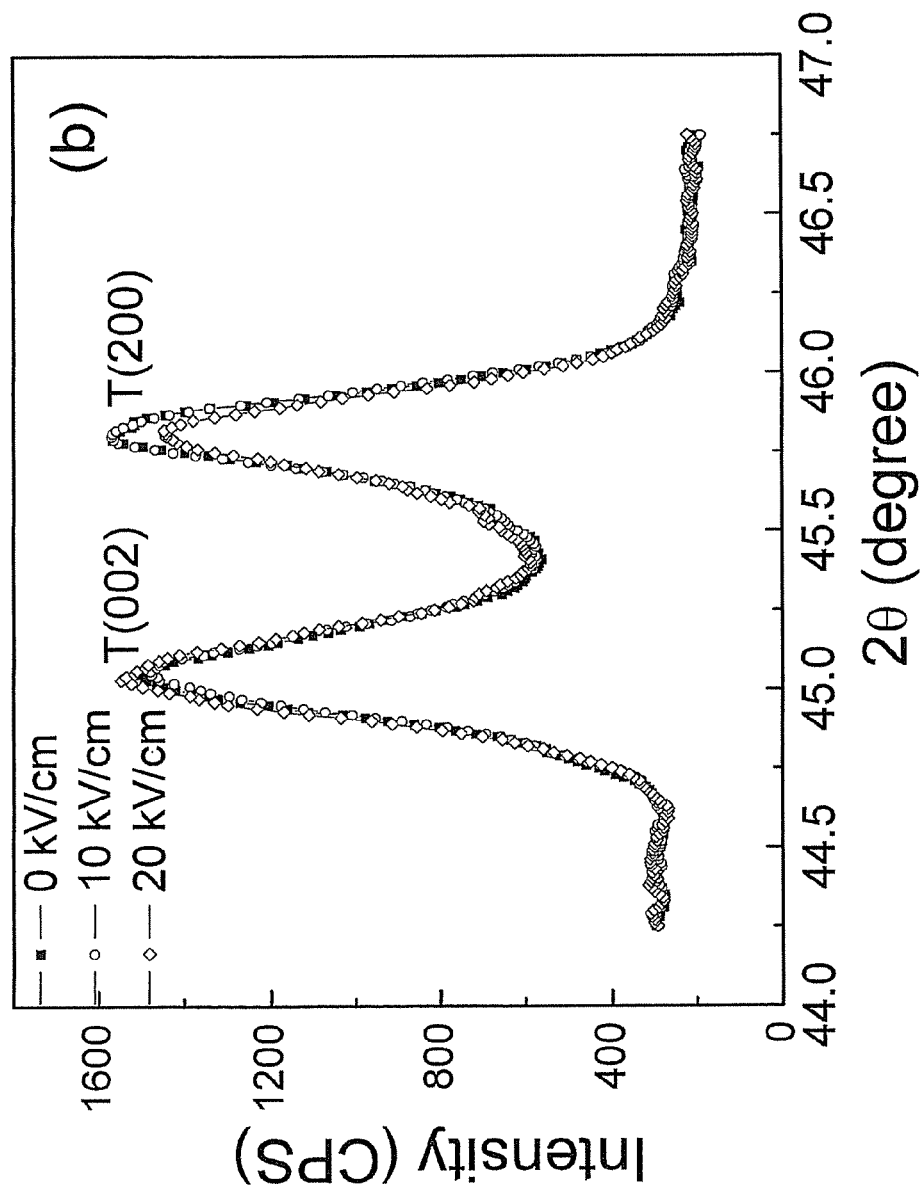

A 0 kV/cm, 5 kV/cm, 10 kV/cm, 15 kV/cm and 20 kV/cm electric field was applied to the Sb—NKNLN free standing film and bulk bar under various experimental conditions. FIGS. 7(a)-7(b) shows the in-situ XRD of the unpoled Sb—NKNLN free standing film and the bulk bar. Before poling, the free standing film showed XRD peak intensity changed due to domain switching as electric field increased over a range of 0 kV/cm to 20 kV/cm. However, for the bulk material, the XRD pattern remained essentially unchanged up to about 20 kV/cm. The results for an applied electric field at 5 kV/cm and 15 kV/cm are similar to that disclosed in FIG. 7(b).

Figure 8A:
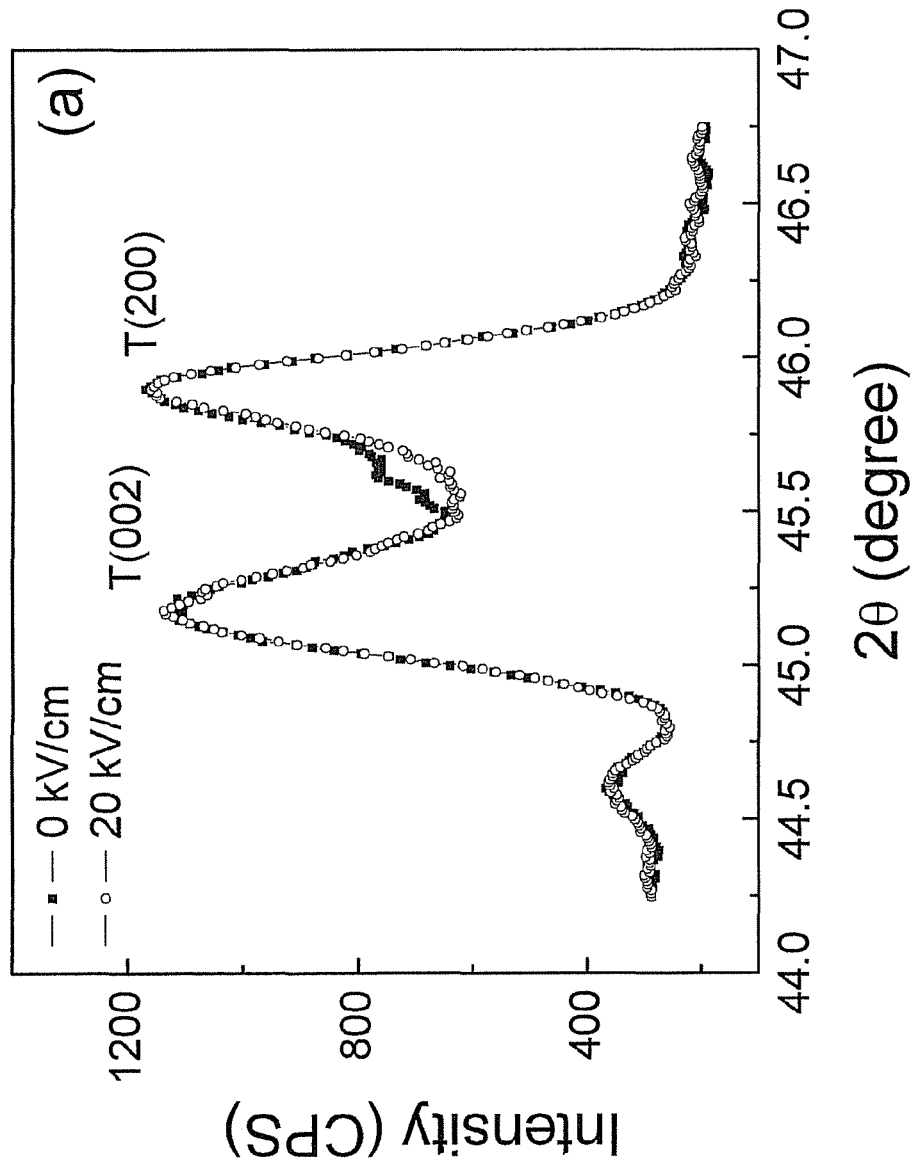
FIG. 8(*a*) is a graph of in-situ XRD peaks of tetragonal (002) and (200) of the poled Sb—NKNLN free-standing film when the external electric field was applied along the poling direction.
Figure 8B:
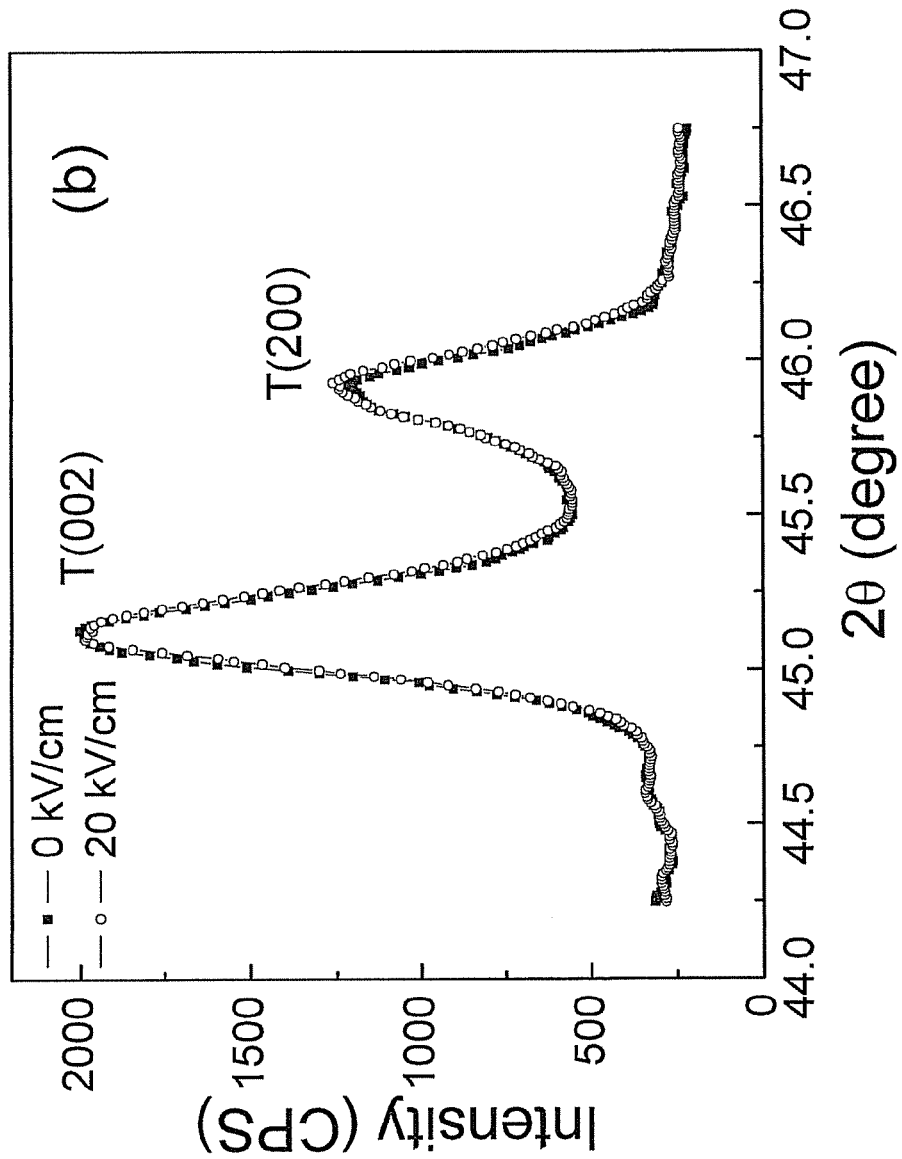

After poling, the intensities of the tetragonal peak (002) and tetragonal peak (200) significantly changed. The (002) peak grew much stronger as many domains switched from a-oriented to c-oriented. As shown in FIGS. 8(a)-8(b), when a positive electric field was applied along the poling direction, no appreciable change was observed for either the free standing films or the bulk bar. The results for an applied electric field at 5 kV/cm, 10 kV/cm and 15 kV/cm in FIGS. 8(a) and 8(b) are similar to the curves disclosed in FIGS. 8(a) and 8(b) respectively.

Figure 9A:
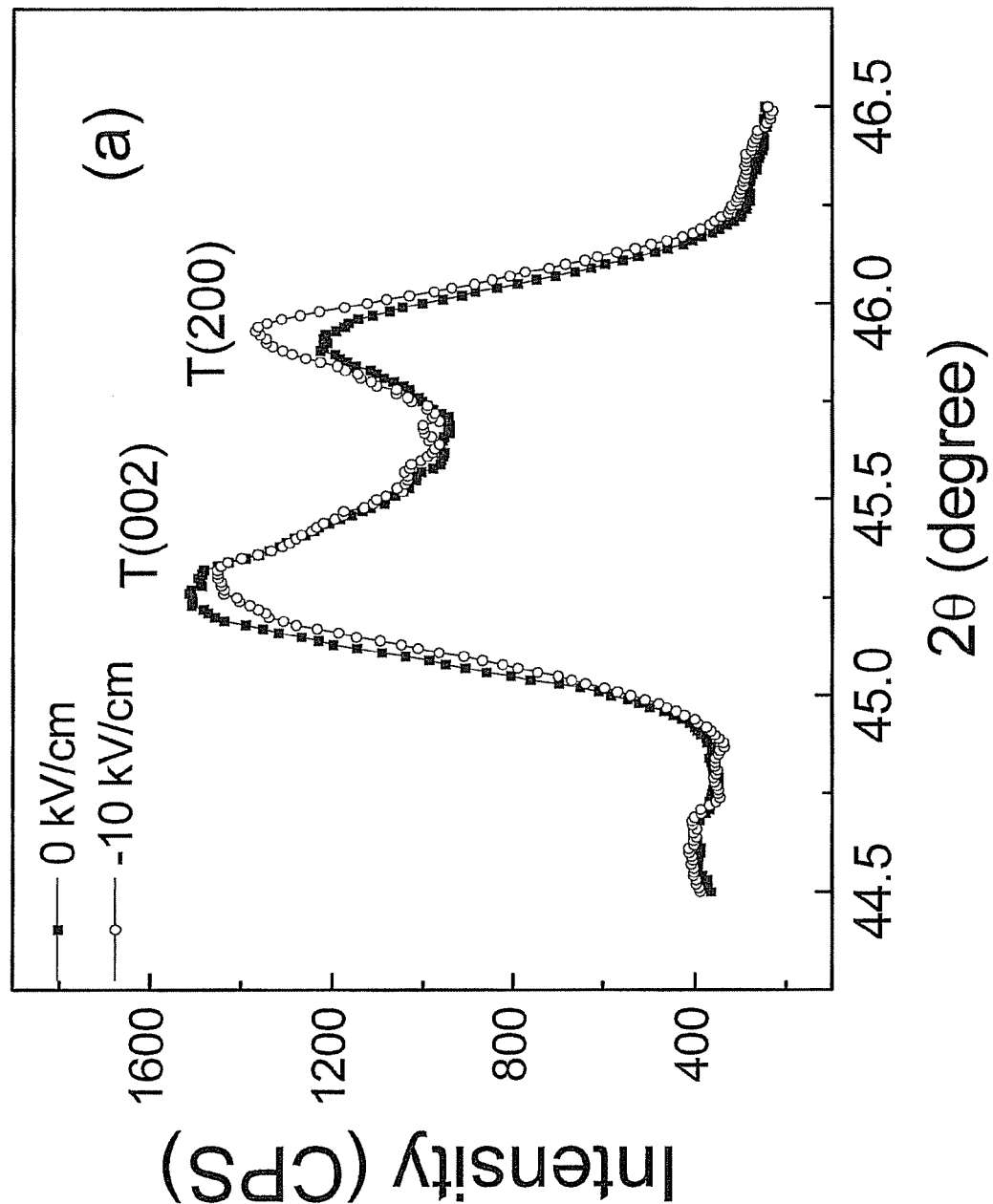
FIG. 9(*a*) is a graph of in-situ XRD peaks of tetragonal (002) and (200) of the poled Sb—NKNLN free-standing film when the external electric field was applied in the direction opposite to the poling direction.
Figure 9B:
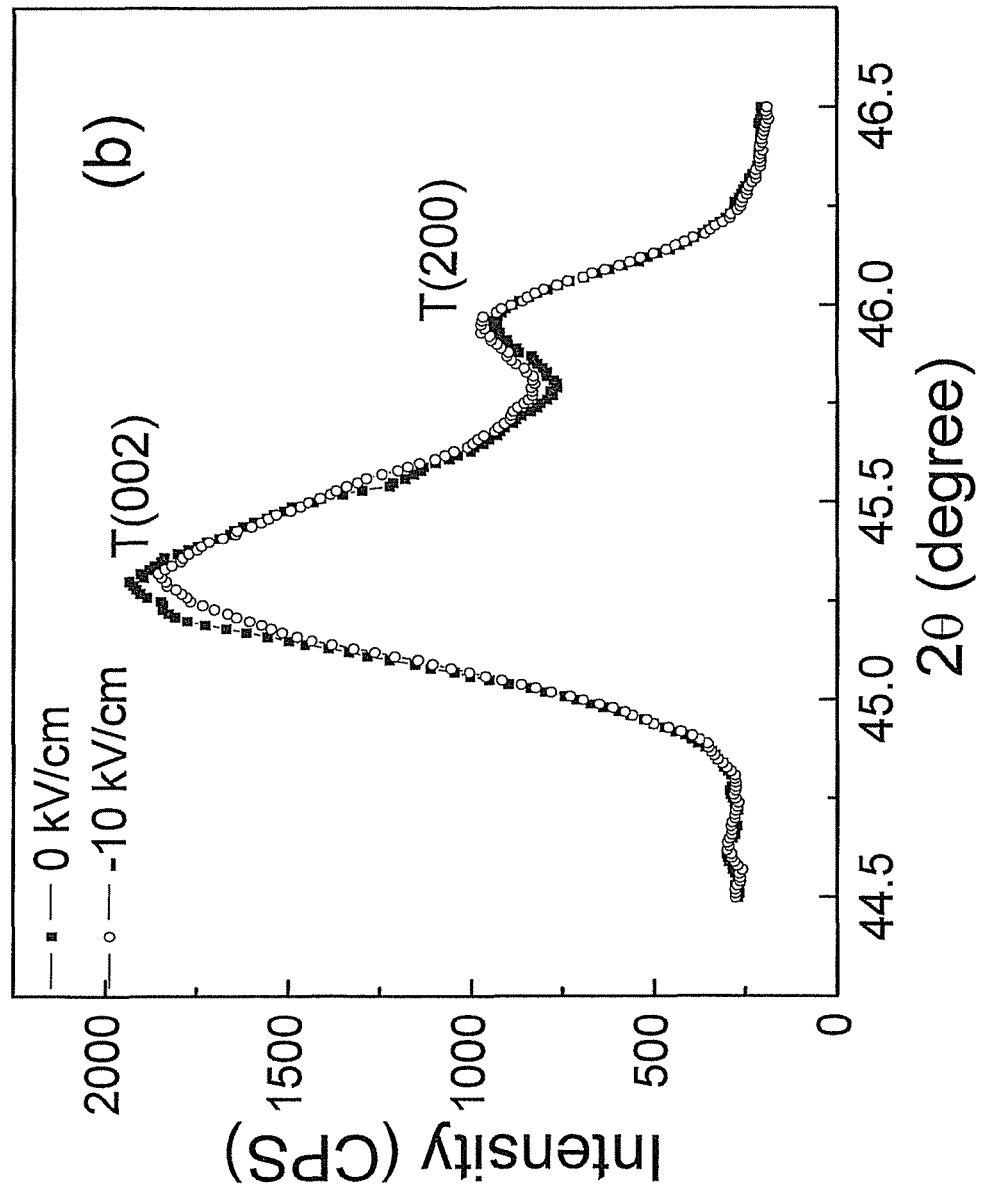

However, when the electric field was applied in a direction opposite to the poling direction, a peak intensity change was observed in the free standing film at 10 kV/cm, whereas the bulk bar still showed no change, as shown in FIGS. 9(a)-9(b). The results for an applied electric field at −5 kV/cm, −15 kV/cm and −15 kV/cm in FIGS. 9(a) and 9(b) are similar to the curves disclosed in FIGS. 9(a) and 9(b) respectively. The in-situ XRD results in FIGS. 8(a)-8(b) and FIGS. 9(a)-9(b) are consistent with the dielectric constant behavior of the free standing film and the bulk bar under an electric field, which suggests that the free standing film geometry enables easier domain switching.

The invention claimed is:

1. A free standing film that is substantially lead-free, wherein the free standing film is produced from a lead-free piezoelectric material selected from the group consisting of solid solutions comprising one or more of $(Bi_{0.5}K_{0.5})TiO_3$, $(Bi_{0.5}Na_{0.5})TiO_3$, $Ba(Zr_xTi_{1-x})O_3$, $BaTiO_3$, $(Bi_{1/2}K_{1/2})TiO_3$, $(Bi_{1/2}Na_{1/2})TiO_3$, $Ba(Zr_xTi_{1-x})O_3$, $Bi(Zn_{1/2}Ti_{1/2})O_3$, $(Na_xK_{1-x})NbO_3$, $BiScO_3$—$PbTiO_3$ $BaTiO_3$—$(Bi_{1/2}K_{1/2})TiO_3$, $(Bi_{1/2}Na_{1/2})TiO_3$—$(Bi_{1/2}K_{1/2})TiO_3$, $(Bi_{1/2}Na_{1/2})TiO_3$—$BaTiO_3$, $(Bi_{1/2}Na_{1/2})TiO_3$—$Ba(Zr_xTi_{1-x})O_3$ and $(Bi_{1/2}Na_{1/2})TiO_3$—$BaTiO_3$—$(Bi_{1/2}K_{1/2})TiO_3$.

2. The film of claim 1, wherein said film has a piezoelectric coefficient $-d_{31}$ of about 200 pm/V to about 2000 pm/V.

3. The film of claim 1, wherein said piezoelectric coefficient $-d_{31}$ is about 1500 pm/V to about 1800 pm/V.

4. The film of claim 1, wherein said piezoelectric coefficient $-d_{31}$ is about 1600 pm/V to about 1700 pm/V.

5. The film of claim 1, wherein said film has a thickness of about 4 μm to about 100 μm.

6. The film of claim 2, wherein the free standing film exhibits asymmetrical non-180° domain switching.

7. A microelectronic device comprising a piezoelectric layer produced from a film as claimed in claim 1.

8. A microelectronic device comprising a piezoelectric layer produced from a film as claimed in claim 2.

9. The film of claim 8, wherein said microelectronic device is selected from the group consisting of: an energy harvesting device and a piezoelectric sensor.

10. A piezoelectric sensor comprising:
a non-piezoelectric layer;
a lead-free piezoelectric layer comprising a material selected from the group consisting of: $(Na_{0.5}K_{0.5})_{0.945}Li_{0.055}Nb_{0.96}Sb_{0.04}O_3$, $Sb$—$(Na_{0.5}K_{0.5})NbO_3$—$LiTaO_3$, $Sr$—$(Na_{0.5}K_{0.5})NbO_3$—$LiTaO_3$, $Sr$—$Na_{0.5}K_{0.5})NbO_3$—$LiTaO_3$, $SbSr$—$(Na_{0.5}K_{0.5})NbO_3$—$LiTaO_3$, $SrSb$—$Na_{0.5}K_{0.5})NbO_3$—$LiTaO_3$, $(Bi_{0.5}K_{0.5})TiO_3$, $(Bi_{0.5}Na_{0.5})TiO_3$, $Ba(Zr_xTi_{1-x})O_3$, $BaTiO_3$, $(Bi_{1/2}K_{1/2})TiO_3$, $(Bi_{1/2}Na_{1/2})TiO_3$, $Ba(Zr_xTi_{1-x})O_3$, $Bi(Zn_{1/2}Ti_{1/2})O_3$, $(Na_xK_{1-x})NbO_3$, $BiScO_3$—$PbTiO_3$ $BaTiO_3$—$(Bi_{1/2}K_{1/2})TiO_3$, $(Bi_{1/2}Na_{1/2})TiO_3$—$(Bi_{1/2}K_{1/2})TiO_3$, $(Bi_{1/2}Na_{1/2})TiO_3$—$BaTiO_3$, $(Bi_{1/2}Na_{1/2})TiO_3$—$Ba(Zr_xTi_{1-x})O_3$, $(Bi_{1/2}Na_{1/2})TiO_3$—$BaTiO_3$—$(Bi_{1/2}K_{1/2})TiO_3$ and mixtures thereof;
at least one conducting element operatively associated with the lead-free piezoelectric layer; and
a receptor capable of binding a molecule or compound whereby, upon binding, said molecule or compound exerts a force on the piezoelectric layer;
wherein the said lead-free piezoelectric layer has a piezoelectric coefficient $-d_{31}$ of about 200 pm/V to about 2000 pm/V.

11. The sensor of claim 10, wherein said piezoelectric coefficient $-d_{31}$ is about 1500 pm/V to about 1800 pm/V.

12. The sensor of claim 10, wherein said piezoelectric coefficient $-d_{31}$ is about 1600 pm/V to about 1700 pm/V.

13. The sensor of claim 10, further comprising an electrical insulation layer which insulates the conducting elements.

14. The sensor of claim 10, wherein the electrical insulation layer comprises a material selected from the group consisting of poly-para-xylylene, methyltrimethoxysilane, $Al_2O_3$, $SiO_2$ and functionalized hydrophobic silanes and mixtures thereof.

15. The sensor of claim 14, wherein said receptor is bound to the conducting element by an immobilization layer.

16. The sensor of claim 10, wherein said lead-free piezoelectric layer further comprises at least one additional piezoelectric property-enhancing dopant.

17. The sensor of claim 16, wherein said dopant contains Sb and the lead-free piezoelectric material comprises from about 3% to about 6% Sb.

18. The sensor of claim 10, wherein the lead-free piezoelectric layer comprises a compound containing at least one element selected from the group consisting of: Sb, Sr, Ba, V and Bi.

19. The sensor of claim 10, wherein the lead-free piezoelectric layer comprises an antimony compound.

20. The sensor of claim 10, wherein the lead-free piezoelectric layer comprises a cation selected from the group consisting of: Li, Na and K cations.

* * * * *